United States Patent [19]

Ballinger et al.

[11] Patent Number: 5,780,285
[45] Date of Patent: *Jul. 14, 1998

[54] SUBTILISIN VARIANTS CAPABLE OF CLEAVING SUBSTRATES CONTAINING DIBASIC RESIDUES

[75] Inventors: Marcus D. Ballinger; James A. Wells. both of Burlingame, Calif.

[73] Assignee: Genentech, Inc., South San Francisco, Calif.

[*] Notice: The term of this patent shall not extend beyond the expiration date of Pat. No. 5.741.664.

[21] Appl. No.: 398,028

[22] Filed: Mar. 3, 1995

[51] Int. Cl.⁶ .............................. C12N 9/54; C12N 9/56; C12N 15/57; C12N 15/75
[52] U.S. Cl. ............... 435/222; 435/69.1; 435/172.3; 435/221; 435/252.3; 435/252.31; 435/320.1; 536/23.2
[58] Field of Search ................... 435/221, 222, 435/69.1, 172.3, 252.3, 252.31, 320.1, 68.1; 536/23.2

[56] References Cited

U.S. PATENT DOCUMENTS

| 4,760,025 | 7/1988 | Estell et al. ............... 435/222 |
| 5,371,008 | 12/1994 | Carter et al. ............... 435/222 |

FOREIGN PATENT DOCUMENTS

| 251 446 | 2/1988 | European Pat. Off. . |
| 316748 | 5/1989 | European Pat. Off. . |
| 405901 | 1/1991 | European Pat. Off. . |
| 0 130 756 | 6/1991 | European Pat. Off. . |
| WO 91/11454 | 8/1991 | WIPO . |
| WO 92/02615 | 2/1992 | WIPO . |
| WO 95/30010 | 11/1995 | WIPO . |

OTHER PUBLICATIONS

Bode et al., "Refined 1.2 A crystal structure of the complex formed between subtilisin Carlsberg and the inhibitor eglin c. Molecular structure of eglin and its detailed interaction with subtilisin" *EMBO Journal* 5(4) :813–818 (1986).

Brenner et al., "Sturctural and enzymatic characterization of a purified prohormone-processing enzyme: Secreted, coluble Kex2 protease" *Proc. Natl. Acad. Sci. USA* 89:922–926 (1992).

Breshnahan, P.A. et al., "Human fur gene encodes a yeast kex2-like endoprotease that cleaves pro–β–NGF in vivo" *Journal of Cell Biology* 111 (6, Pt 2) :2851–2859 (1990).

Carter et al., "Engineering Subtilisin BPN' for Site–Specific Proteolysis" *Proteins: Struct. Funct., Genet.*6:240–248 (1989).

Creemers et al., "Modulation of Furin–Mediated Proprotein Processing Activity by Site–directed Mutagenesis" *The Journal of Biological Chemistry* 268(29) :21826–21834 (1993).

(List continued on next page.)

*Primary Examiner*—Robert A. Wax
*Assistant Examiner*—William W. Moore
*Attorney, Agent, or Firm*—Jeffrey S. Kubinec

[57] ABSTRACT

The bacterial serine protease, subtilisin BPN', has been mutated so that it will efficiently and selectively cleave substrates containing dibasic residues. A combination mutant, where Asn 62 was changed to Asp and Gly 166 was changed to Asp (N62D/G166D), had a larger than additive shift in specificity toward dibasic substrates. Suitable substrates of the variant subtilisin were revealed by sorting a library of phage particles (substrate phage) containing five contiguous randomized residues. This method identified a particularly good substrate, Asn-Leu-Met-Arg-Lys-, that was selectively cleaved in the context of a fusion protein by the N62D/G166D subtilisin variant. Accordingly, this variant subtilisin may be useful for cleaving fusion proteins with dibasic substrate linkers and processing hormones or other proteins (in vitro or in vivo) that contain dibasic cleavage sites.

1 Claim, 19 Drawing Sheets

OTHER PUBLICATIONS

Eder et al., "Hydrolysis of Small Peptide Substrates Parallels Binding of Chymotrypsin Inhibitor 2 for Mutants of Subtilisn BPN'" *Federation of European Biochemical Societies* 335(3) :349–352 (1993).

Forsberg et al., "An Evaluation of Different Enzymatic Cleavage Methods for Recombination Fusion Proteins, Applied on Des (1–3) Insulin–Like Growth Factor I" *Journal of Protein Chemistry* 11(2) :201–211 (1992).

Graf et al., "Electrostatic Complementarity Within the Substrate–Binding Pocket of Trypsin" *Proc. Natl. Acad. Sci.* 85:4961–4965 (1988).

Hedstrom et al., "Converting Trypsin to Chymotrypsin: The Role of Surface Loops" *Science*, 255(5049) :1249–1253 (1992).

Hosaka et al., "Arg–X–Lys/Arg–Arg Motif as a Signal for Precursor Cleavage Catalyzed by Furin within the Constitutive Secretory Pathway" *Journal of Biological Chemistry* 266(19) :12127–12130 (1991).

Hwang et al., "Why ION Pair Reversal by Protein Engineering is Unlikely to Succeed" *Nature* 334:270–272 (1988).

Kraut, Joseph, "Serine Proteases: Structure and Mechanism of Catalysis" *Ann. Rev. Biochem.* 46:331–358 (1977).

Lipkind et al., "Molecular Modeling of the Substrate Specificity of Prohormone Convertases SPC2 and SPC3" *The Journal of Biological Chemistry* 270 (22) :13277–13284 (1995).

Matthews et al., "A Survey of Furin Substrate Specificity Using Substrate Phage Display" *Protein Science* 3:1197–1205 (1994).

Matthews et al., "X–ray Crystallographic Study of Boronic Acid Adducts with Subtilisin BPN' (Novo)" *Journal of Biological Chemistry* 250 (18) : 7120–7126 (1975).

McPhalen et al., "Structural Comparison of Two Serine Proteinase–Protein Inhibitor Complexes: Eglin–C–Subtilisin Carlsberg and CI–2–Subtilisin Novo" *Biochemistry* 27:6582–6598 (1988).

Philipp et al., "Kinetics of Subtilisin and Thiolsubtilisin" *Molecular and Cellular Biochemistry* 51(5): 5–32 (1983).

Poulos et al., "Polypeptide Halomethyl Ketones Bind to Serine Proteases as Analogs of the Tetrahedral Intermediate" *The Journal of Biological Chemistry* pp. 1097–1103 (1975).

Rheinnecker et al., "Engineering a Novel Specificity in Subtilisin BPN'" *Biochemistry* 32(5) :1199–1203 (1993).

Rheinnecker et al., "Variants of Subtilisin BPN' with Altered Specificity Profiles" *Biochemistry* 33 :221–225 (1994).

Robertus et al., "Subtilisin; a Stereochemical Mechanism Involving Transition–State Stabilization" *Biochemistry* 11:4293–4303 (1972).

Robertus et al., "An X–Ray Crystallographic Study of the Binder of Peptide Choloromethyl Ketone Inhibitors to Subtilisin BPN'" *Biochemistry* 11 (13) :2439–2449 (1972).

Russell et al., "Rational modification of enzyme catalysis by engineering surface charge" *Nature* 328:496–500 (1987).

Siezen et al., "Homology Modelling and Protein Engineering Strategy of Subtilases, the Family of Subtilisin–Like Serine Proteinases" *Protein Engineering* 4(7) :719–737 (1991).

Siezen et al., "Homology Modelling of the Catalytic Domain of Human Furin, a Model for the Eukaryotic Subtilisin–Like Proprotein Convertases" *FEBS Letter* pp. 255–266 (1994).

Smeekens, Steven P., "Processing of Protein Precursors by a Novel Family of Subtilisin–Related Mammalian Endoproteases" *Bio/Technology* 11:182–186 (1993).

Stauffer et al., "The Effect on Subtilisin Activity of Oxidizing a Methionine Residue" *The Journal of Biological Chemistry* 244 (19) :5333–5338 (1969).

Steiner et al., "The New Enzymology of Precursor Processing Endoproteases" *Journal of Biological Chemistry* 267(33) :23435–23438 (1992).

Stennicke et al., "Effects of introduced aspartic and glutamic acid residues on the P'1 substrate specificity, pH dependence and stability of carboxpeptidase Y" *Protein Engineering* 7(7) :911–916 (1994).

Svendsen, I., "Chemical Modifications of The Subtilisins With Specific Reference to the Binding of Large Substrates. A Review." *Carlsberg Rs. Commu.* 41(5) :237–291 (1976).

Wells et al., "Cloning, sequencing, and secretion of Bacillus amyloliquefaciens subtilisin in Bacillus subtilis" *Nucleic Acid Research* 11(22) :7911–7929 (1983).

Wells et al., "Designing substrate specificity by protein engineering of electrostatic interactions" *Proc. Natl. Acad. Sci USA* 84:1219–1223 (1987).

Wise et al., "Expression of a human proprotein processing enzyme: correct cleavage of the von Willebrand factor precursor at a paired basic amino acid site" *Proc. Natl. Acad. Sci. USA* 87:9378–9382 (1990).

Wright et al., "Structure of Subtilisin BPN' at 2–5 A Resolution" *Nature* 221:235–242 (1969).

Drenth et al., "Subtilisin Novo; The Three–Dimensional Structure and Its Comparison with Subtilisin BPN'" *European Journal of Biochemistry* 26:177–181 (1972).

Knauf et al., "Relationship of Effective Molecular Size to Systemic Clearance in Rats of Reconbinant Interleukin–2 Chemically Modified with Water Soluble Polymers" *The Journal of Biolgical Chemistry* 29 (Oct. 15) :15064–15070 (1988).

Estell et al., "Probing Steric and Hydrophobic Effects on Enzyme–Substrate Interactions by Protein Engineering" *Science* 233:659–663 (1986).

Graycar et al., "Altering the Proteolytic Activity of Subtilisin through Protein Engineering" *Annals of the New York Academy of Sciences* 672:71–79 (1992).

Nakayama et al., "Consensus Sequence for Precursor Processing at Mono–arginyl Sites" *Journal of Biological Chemistry* 267:16335–16340 (1992).

Wells et al., "Recruitment of Substrate–specificity Properties from One Enzyme Into a Related One by Protein Engineering" *Proc. Natl. Acad. Sci. USA* 84:5167–5171 (1987).

Wells et al., "Subtilisin: An Enzyme Made for Engineering" *J. Cell. Biochem.* (abstract B7–0120 Suppl. 19B:233 (1995).

```
                                                                    ahaII/draI
                      nspBII       claI/bspI06
505  GTA GCG GTT ATC GAC AGC GGT ATC GAT TCT TCT CAT CCT GAT TTA AAG GTA GCA GGC GGA GCC AGC ATG GTT CCT TCT GAA
     CAT CGC CAA TAG CTG TCG CCA TAG CTA AGA AGA GTA GGA CTA AAT TTC CAT CGT CCG CCT CGG TAC CAA GGA AGA CTT
     Val Ala Val Ile Asp Ser Gly Ile Asp Ser Ser His Pro Asp Leu Lys Val Ala Gly Gly Ala Ser Met Val Pro Ser Glu
                        30                                40                                50 naeI
                                 cfr10I
586  ACA AAT CCT TTC CAA GAC AAC TCT CAC GGA ACT CAC GTT CTC GGT GCC GGC ACA GTT GCC GCT CTT AAT AAC TCA ATC GGT GTA
     TGT TTA GGA AAG GTT CTG TTG AGA GTG CCT TGA GTG CAA GAG CCA CGG CCG TGT CAA CGG CGA GAA TTA TTG AGT TAG CCA CAT
     Thr Asn Pro Phe Gln Asp Asn Ser His Gly Thr His Val Ala Gly Thr Val Ala Ala Leu Asn Asn Ser Ile Gly Val
                              60                                70                                80 eaeI       pvuII
                                                                  cfrI       nspBII
667  TTA GGC GTT GCG CCA AGC GCA TCA CTT TAC GCT GTA AAA GTT CTC GGT GCT GAC GGT TCC GGC CAA TAC AGC TGG ATC ATT
     AAT CCG CAA CGC GGT TCG CGT AGT GAA ATG CGA CAT TTT CAA GAG CCA CGA CTG CCA AGG CCG GTT ATG TCG ACC TAG TAA
     Leu Gly Val Ala Pro Ser Ala Ser Leu Tyr Ala Val Lys Val Leu Gly Ala Asp Gly Ser Gly Gln Tyr Ser Trp Ile Ile
                           90                                100 pvuI/bspCI
            mcrI                                                                                     ahaIII/draI
748  AAC GGA ATC GAG TGG GCG ATC GCA AAC AAT ATG GAC GTT ATT AAC ATG AGC CTC GGC CCT TCT GGT TCT GCT GCT TTA
     TTG CCT TAG CTC ACC CGC TAG CGT TTG TTA TAC CTG CAA TAA TTG TAC TCG GAG CCG GGA AGA CCA AGA CGA CGA AAT
     Asn Gly Ile Glu Trp Ala Ile Ala Asn Asn Met Asp Val Ile Asn Met Ser Leu Gly Pro Ser Gly Ser Ala Ala Leu
                        110                               120                               130 salI
                                                                                                     hincII/hindII
           hinfI/acyI                                                                                accI
           ahaII/bsaHI
829  AAA GCC GCA GTT GAT AAA GCC GGT GTC GTA TCC GGC GTC GTT GCG GCA GCC GGT AAC GAA GGC ACT TCC GGC AGC TCG
     TTT CGG CGT CAA CTA TTT CGG CCA CAG CAT AGG CCG CAG CAA CGC CGT CGG CCA TTG CTT CCG TGA AGG CCG TCG AGC
     Lys Ala Ala Val Asp Lys Ala Gly Val Val Val Val Ala Ala Gly Asn Glu Gly Thr Ser Gly Ser Ser
                     140                               150                               160 haeII   hincII/hindII           cfr10I
910  TCG ACA GTG GAC TAC CCT GGC AAA TAC CCT GTC ATT GCA GTA GGC GCT GTT GAC GTA AGC AAC CAA AGA GCA TCT TTC
     AGC TGT CAC CTG ATG GGA CCG TTT ATG GGA CAG TAA CGT CAT CCG CGA CAA CTG CAT TCG TTG GTT TCT CGT AGA AAG
     Ser Thr Val Asp Tyr Pro Gly Lys Tyr Pro Val Ile Ala Val Gly Ala Val Asp Ser Asn Gln Arg Ala Ser Phe
                  170                               180
```

```
                                         hgiCI
                        ppuMI             banI
              eco0109I/draII
 991 TCA AGC GTA GGA CCT GAG CTT GAT GTC GCA CCT GGC GTA TCT ATC CAA AGC ACG CTT CCT GGA AAC TAC GGG GCG
     AGT TCG CAT CCT GAA CTC GTA CAG CGT GGA CCG CAT AGA TAG GTT TCG TGC GAA CCT TTG ATG CCC CGC
     Ser Val Gly Pro Glu Leu Asp Val Met Ala Pro Gly Val Ser Ile Gln Ser Thr Leu Pro Gly Asn Lys Tyr Gly Ala
     190                                         200                                         210 kpnI
              hgiCI
              banI
              asp718
              acc65I                bglI bsrBI
1072 TAC AAC GGT ACC TCA ATG GCA TCT CCG CAC GTT GGA GCG GCT TTG ATT CTT TCT AAG CAC CCG AAC TGG ACA AAC
     ATG TTG CCA TGG AGT TAC CGT AGA GGC GTG CAA CCT CGC CGA AAC TAA GAA AGA TTC GTG GGC TTG ACC TGT TTG
     Tyr Asn Gly Thr Ser Met Ala Ser Pro His Val Gly Ala Ala Leu Ile Leu Ser Lys His Pro Asn Trp Thr Asn
                     220                                         230                                   240 bclI(dam-)
1153 ACT CAA GTC CGC AGC AGT TTA GAA AAC ACC ACT ACA AAA CTT GGT GAT TCT TTC AAG ATG GGG CTG ATC AAC GTA
     TGA GTT CAG GCG TCG TCA AAT CTT TTG TGG TGA TGT TTT GAA CCA CTA AGA ATA CCT TTT CCC GAC TAG TTG CAT
     Thr Gln Val Arg Ser Ser Leu Glu Asn Thr Thr Thr Lys Leu Gly Asp Ser Phe Lys Met Gly Leu Ile Asn Val
                         250                                         260                              270 styI                        nspI
                                              cfr10I                      nspHI    bsrBI
1234 CAG GCG GCA GCT CAG TAA AACATAAAA AACCGGCCTT GGCCCCGCCG GTTTTTTATT ATTTTTCTTC CTCCGCATGT TCAATCCGCT
     GTC CGC CGT CGA GTC ATT TTGTATTTT TTGGCCGGAA CCGGGCGGC CAAAAAATAA TAAAAAGAAG GAGGCGTACA AGTTAGGCGA
     Gln Ala Ala Ala Gln Oc* eaeI
                                         apoI         hincII/hindII       cfrI                       esp3I
1321 CCATAATCGA CGGATGGCTC CCTCTGAAAA TTTTAACGAG AAACGGGCGG TTGACCCGGG TCAGTCCCGT AACGGCCAAG TCCTGAAACG TCTCAATCGC
     GGTATTAGCT GCCTACCGAG GGAGACTTTT AAAATTGCTC TTTGCCCGCC AACTGGGCCC AGTCAGGGCA TTGCCGGTTC AGGACTTTGC AGAGTTAGCG
```

FIG. 6C

```
                    bsaWI                    mcrI                       esp3I bsmI                                        mroI
                                                                                                                          bspMII
                                                                                                                          bspEI(dam-)
                                                                                                                          bsaWI
                                                                                                                          accIII(dam-)
                                                                                                                          bstYI/xhoII
                                                                                                                          bamHI           psp14061
1421 CGCTTCCCGG TTTCCGGTCA GCTCAATGCC GTAACGGTCG GCGGCGTTTT CCTGATACCG GGAGACGGCA TTCGTAATCG GATCCGGAAA TTGTAAACGT
     GCGAAGGGCC AAAGGCCAGT CGAGTTACGG CATTGCCAGC CGCCGCAAAA GGACTATGGC CCTCTGCCGT AAGCATTAGC CTAGGCCTTT AACATTTGCA sspI             apoI       apoI
1521 TAATATTTTG TTAAAATTCG CGTTAAATTT TTGTTAAATC AGCTCATTTT TTAACCAATA GGCCGAAATC GGCAAAATCC CTTATAAATC AAAAGAATAG
     ATTATAAAAC AATTTTAAGC GCAATTTAAA AACAATTTAG TCGAGTAAAA AATTGGTTAT CCGGCTTTAG CCGTTTTAGG GAATATTTAG TTTTCTTATC drdI
1621 ACCGAGATAG GGTTGAGTGT TGTTCCAGTT TGGAACAAGA GTCCACTATT AAAGAACGTG GACTCCAACG TCAAAGGGCG AAAAACCGTC TATCAGGGCT
     TGGCTCTATC CCAACTCACA ACAAGGTCAA ACCTTGTTCT CAGGTGATAA TTTCTTGCAC CTGAGGTTGC AGTTTCCCGC TTTTTGGCAG ATAGTCCCGA hgiJII
                                                                                                     bsp1286
                                              hgiCI                                                  bmyI
                   bsaAI                      banI                                                   banII
                   draIII
1721 ATGGCCCACT ACGTGGAACCA TCACCCTAAT CAAGTTTTTT GGGGTCGAGG TGCCGTAAAG CACTAAATCG GAACCCTAAA GGGAGCCCCC GATTTAGAGC
     TACCGGGTGA TGCACTTGGT AGTGGGATTA GTTCAAAAAA CCCCAGCTCC ACGGCATTC GTGATTTAGC CTTGGGATTT CCCTCGGGGG CTAAATCTCG naeI                                            haeII
         cfr10I                                bsrBI            haeII
1821 TTGACGGGGA AAGCCGGCGA ACGTGGCGAG AGGAGCGGG AAGAAAGCGA AAGGAAGGG CGCTAGGGCG CTGGCAAGTG TAGCGGTCAC GCTGCGCGTA
     AACTGCCCCT TTCGGCCGCT TGCACCGCTC TGCCACCGCTC TTCTTTCGCT TTCCTTCCC GCGATCCCGC GACCGTTCAC ATCGCCAGTG CGACGCGCAT
```

FIG. 6D

```
                                                     mroI
                                                     bspMII
                                                     bspEI(dam-)
                                                     bsaWI                              haeI
                               scfI   accIII(dam-)
1921 ACCACCACAC CCGCCGCGCT TAATGCGCCG CTACAGGGCG CGTCCGGATC XGATCCGACG CGAGGCTGGA TGGCCTTCCC CATTATGATT CTTCTCGCTT
     TGGTGGTGTG GGCGGCGCGA ATTACGCGGC GATGTCCCGC GCAGGCCTAG ?CTAGGCTGC GCTCCGACCT ACCGGAAGGG GTAATACTAA GAAGAGCGAA haeI                                     bspMI
2021 CCGGCGGGCAT CGGGATGCCC GCGTTGCAGG CCATGCTGTC CAGGCAGGTA GATGACGACC ATCAGGGACA GCTTCAAGGA TCGCTCGCGG CTCTTACCAG
     GGCCGCCCGTA GCCCTACGGG CGCAACGTCC GGTACGACAG GTCCGTCCAT CTACTGCTGG TAGTCCCTGT CGAAGTTCCT AGCGAGCGCC GAGAATGGTC narI
                                                                                                 kasI
                                                                                                 hinlI/acyI
                                                           hgiAI/aspHI                           hgiCI
                                                           bsp1286                               haeII
                                                           bsiHKAI                               banI
                                 nspBII                    bmyI                                  ahaII/bsaHI
2121 CCTAACTTCG ATCACTGGAC CGCTGATCGT CACGGCGATT TATGCCGCCT CGGCGAGCAC ATGGAACGGG TTGGCATGGA TTGTAGGCGC CGCCCTATAC
     GGATTGAAGC TAGTGACCTG GCGACTAGCA GTGCCGCTAA ATACGGCGGA GCCGCTCGTG TACCTTGCCC AACCGTACCT AACATCCGCG GCGGGATATG hgiCI                           pflMI
                                                                      nael     banI
                                                                      cfr10I
2221 CTTGTCTGCC TCCCCGCGTT GCGTCGCGGT GCATGGAGCC GGGCCACCTC GACCTGAATG GAAGCCGGCG GCACCTCGCT AACGGATTCA CCACTCCAAG
     GAACAGACGG AGGGGCGCAA CGCAGCGCCA CGTACCTCGG CCCGGTGGAG CTGGACTTAC CTTCGGCCGC CGTGGAGCGA TTGCCTAAGT GGTGAGGTTC mstI
                             avilI/fspI  styI
                             bsmI        pflMI                                               gsuI/bpmI
2321 AATTGGAGCC AATCAATTCT TGCGGAGAAC TGTGAATGCG CAAACCAACC CTTGGCAGAA CATATCCATC GCGTCCGCCA TCTCCAGCAG CCGCACGCGG
     TTAACCTCGG TTAGTTAAGA ACGCCTCTTG ACACTTACGC GTTTGGTTGG GAACCGTCTT GTATAGGTAG CGCAGGCGGT AGAGGTCGTC GGCGTGCGCC avaI                                                                drdI
2421 CGCATCTCGG GCCGCGTTGC TGGCGTTTTT CCATAGGCTC CGCCCCCCTG ACGAGCATCA CAAAAATCGA CGCTCAAGTC AGAGGTGGCG AAACCCGACA
     GCGTAGAGCC CGGCGCAACG ACCGCAAAAA GGTATCCGAG GCGGGGGGAC TGCTCGTAGT GTTTTTAGCT GCGAGTTCAG TCTCCACCGC TTTGGGCTGT
```

FIG. 6E

```
                                                                      bsaWI
2521 GGACTATAAA GATACCAGGC GTTTCCCCCT GGAAGCTCCC TCGTGCGCTC TCCTGTTCCG ACCCTGCCGC TTACCGGATA CCTGTCCGCC TTTCTCCCTT
     CCTGATATTT CTATGGTCCG CAAAGGGGGA CCTTCGAGGG AGCACGCGAG AGGACAAGGC TGGGACGGCG AATGGCCTAT GGACAGGCGG AAAGAGGGAA hgiAI/aspHI
                                                                                                 bsp1286
                                                                                                 bsiHKAI
                                                                                                 bmyI
                                                                                                 apaLI/snoI
              haeII              scfI                                                            alw44I/snoI
2621 CGGGAAGCGT GCGCTTTCT CAATGCTCAC GCTGTAGGTA TCTCAGTTCG GTGTAGGTCG TTCGCTCCAA GCTGGGCTGT GTGCACGAAC CCCCCGTTCA
     GCCCTTCGCA CCGGCAAAGA GTTACGAGTG CGACATCCAT AGAGTCAAGC CACATCCAGC AAGCGAGGTT CGACCCGACA CACGTGCTTG GGGGGCAAGT nspBII
          mcrI      bsaWI
2721 GCCCGACCGC TGCGCCTTAT CCGGTAACTA TCGTCTTGAG TCCAACCCGG TAAGACACGA CTTATCGCCA CTGGCAGCAG CCACTGGTAA CAGGATTAGC
     CGGGCTGGCG ACGCGGAATA GGCCATTGAT AGCAGAACTC AGGTTGGGCC ATTCTGTGCT GAATAGCGGT GACCGTCGTC GGTGACCATT GTCCTAATCG eco57I
                            scfI                      haeI
2821 AGAGCGAGGT ATGTAGGCGG TGCTACAGAG TTCTTGAAGT GGTGGCCTAA CTACGGCTAC ACTAGAAGGA CAGTATTTGG TATCTGCGCT CTGCTGAAGC
     TCTCGCTCCA TACATCCGCC ACGATGTCTC AAGAACTTCA CCACCGGATT GATGCCGATG TGATCTTCCT GTCATAAACC ATAGACGCGA GACGACTTCG nspBII
2921 CAGTTACCTT CGGAAAAAGA GTTGGTAGCT CTTGATCCGG CAAACAAACC ACCGCTGGTA GCGGTGGTTT TTTTGTTGCC AAGCAGCAGA TTACGCGCAG
     GTCAATGGAA GCCTTTTTCT CAACCATCGA GAACTAGGCC GTTTGTTTGG TGGCGACCAT CGCCACCAAA AAAACAAACG TTCGTCGTCT AATGCGCGTC rcaI
          bstYI/xhoII bstYI/xhoII                                                                      bspHI
3021 AAAAAAAGGA TCTCAAGAAG ATCCTTTGAT CTTTTCTACG GGGTCTGACG CTCAGTGGAA CGAAAACTCA CGTTAAGGGA TTTTGGTCAT GAGATTATCA
     TTTTTTTCCT AGAGTTCTTC TAGGAAACTA GAAAAGATGC CCCAGACTGC GAGTCACCTT GCTTTTGAGT GCAATTCCCT AAAACCAGTA CTCTAATAGT ahaIII/draI
     bstYI/xhoII bstYI/xhoII      ahaIII/draI
3121 AAAAAGGATCT TCAACCTAGAT CCTTTTAAAT TAAAAATGAA GTTTTAAATC AATCTAAAGT ATATATGAGT AAACTTGGTC TGACAGTTAC CAATGCTTAA
     TTTTCCTAGA AGTTGGATCTA GGAAAATTTA ATTTTTACTT CAAAATTTAG TTAGATTTCA TATATACTCA TTTGAACCAG ACTGTCAATG GTTACGAATT
```

FIG. 6F

```
                hgiCI                                                              eaml105I
                banI
3221 TCAGTGAGGC ACCTATCTCA GCGATCTGTC TATTTCGTTC ATCCATAGTT GCCTGACTCC CCGTCGTGTA GATAACTACG ATACGGGAGG GCTTACCATC
     AGTCACTCCG TGGATAGAGT CGCTAGACAG ATAAAGCAAG TAGGTATCAA CGGACTGAGG GGCAGCACAT CTATTGATGC TATGCCCTCC CGAATGGTAG gsuI/bpmI
                              bsaI             cfr10I                                      bglI
3321 TGGCCCCAGT GCTGCAATGA TACCGCGAGA CCCACGCTCA CCGGCTCCAG ATTTATCAGC AATAAACCAG CCAGCCGGAA GGGCCGAGCG CAGAAGTGGT
     ACCGGGGTCA CGACGTTACT ATGGCGCTCT GGGTGCGAGT GGCCGAGGTC TAAATAGTCG TTATTTGGTC GGTCGGCCTT CCCGGCTCGC GTCTTCACCA mstI  psp1406I
                           aseI/asnI/vspI                                                avilI/fspI
3421 CCTGCAACTT TATCCGCCTC CATCCAGTCT ATTAATTGTT GCCGGGAAGC TAGAGTAAGT AGTTCGCCAG TTAATAGTTT GCGCAACGTT GTTGCCATTG
     GGACGTTGAA ATAGGCGGAG GTAGGTCAGA TAATTAACAA CGGCCCTTCG ATCTCATTCA TCAAGCGGTC AATTATCAAA CGCGTTGCAA CAACGGTAAC scfI
     pstI                                                          bsaWI
     bsgI                                      pvuI/bspCI                  eaeI
                                               mcrI                        cfrI
3521 CTGCAGGCAT CGTGGTGTCA CGCTCGTCGT TTGGTATGGC TTCATTCAGC TCCGGTTCCC AACGATCAAG GCGAGTTACA TGATCCCCCA TGTTGTGCAA
     GACGTCCGTA GCACCACAGT GCGAGCAGCA AACCATACCG AAGTAAGTCG AGGCCAAGGG TTGCTAGTTC CGCTCAATGT ACTAGGGGGT ACAACACGTT 3621 AAAAGCGGTT AGCTCCTTCG GTCCTCCGAT CGTTGTCAGA AGTAAGTTGG CCGCAGTGTT ATCACTCATG GTTATGGCAG CACTGCCATAA TTCTCTTACT
     TTTTCGCCAA TCGAGGAAGC CAGGAGGCTA GCAACAGTCT TCATTCAACC GGCGTCACAA TAGTGAGTAC CAATACCGTC GTGACGTATT AAGAGAATGA hincII/hindII
                          scaI                                                                          hinlI/acyI
                                                                                        mcrI           ahaII/bsaHI
                                                                                        bcgI
3721 GTCATGCCAT CCGTAAGATG CTTTTCTGTG ACTGGTGAGT ACTCAACCAA GTCATTCTGA GAATAGTGTA TGCGGCGACC GAGTTGCTCT TGCCCGGCGT
     CAGTACGGTA GGCATTCTAC GAAAAGACAC TGACCACTCA TGAGTTGGTT CAGTAAGACT CTTATCACAT ACGCCGCTGG CTCAACGAGA ACGGGCCGCA
```

FIG. 6G

```
                                              hgiAI/aspHI
                                              bsp1286
                                              bsiHKAI                                          bstYI/xhoII
                                              bmyI           xmnI                                          nspBII
                                 ahaII/draI                  asp700
3821 CAACACGGGA TAATACCGCG CCACATAGCA GAACTTTAAA AGTGCTCATC ATTGGAAAAC GTTCTTCGGG GCGAAAACTC TCAAGGATCT TACCGCTGTT
     GTTGTGCCCT ATTATGGCGC GGTGTATCGT CTTGAAATTT TCACGAGTAG TAACCTTTTG CAAGAAGCCC CGCTTTTGAG AGTTCCTAGA ATGGCGACAA hgiAI/aspHI
                      bsp1286
                      bsiHKAI
                      bmyI
                      apaLI/snoI
                      alw44I/snoI    eco57I
     bstYI/xhoII
3921 GAGATCCAGT TCGATGTAAC ACCACTGC CTTTCAGCAT CTTTTACTTT CACCAGCGTT TCTGGGTGAG CAAAACAGG AAGGCAAAAT
     CTCTAGGTCA AGCTACATTG TGGTGACG GGAAGTCGTA GAAAATGAAA GTGGTCGCAA AGACCCACTC GTTTTGTCC TTCCGTTTTA bsrBI
                                                                                                    rcaI
                                                        earI/ksp632I    sspI                        bspHI
4021 GCCGCAAAAA AGGGAATAAAG GGCGACACGG AAATGTTGAA TACTCATACT CTTCCTTTTT CAATATTATT GAAGCATTTA TCAGGGTTAT TGTCTCATGA
     CGGCGTTTTT TCCCTTATTC CCGCTGTGCC TTTACAACTT ATGAGTATGA GAAGGAAAAA GTTATAATAA CTTCGTAAAT AGTCCCAATA ACAGAGTACT hinII/acyI
                                                                             ahaII/bsaHI                rcaI
                                                                             aatII                      bspHI
4121 GCGGATACAT ATTTGAATGT ATTTAGAAAA ATAAACAAAT AGGGGTTCCG CGCACATTTC CCCGAAAAGT GCCACCTGAC GTCTAAGAAA CCATTATTAT
     CGCCTATGTA TAAACTTACA TAAATCTTTT TATTTGTTTA TCCCCAAGGC GCGTGTAAAG GGGCTTTTCA CGGTGGACTG CAGATTCTTT GGTAATAATA bpuAI   aseI/asnI/vspI
              bbsI    xmnI           afIII/bfrI
                                                                                                    ahaIII/draI       psp1406I
           eco109I/draI               asp700
4221 CATGACATTA ACCTATAAAA ATAGGCGTAT CACGAGGCCC TTTCGTCTTC AAGAATTAAT TCCTTAAGGA ACGTACAGAC GGCTTAAAAG CCTTTAAAAA
     GTACTGTAAT TGGATATTTT TATCCGCATA GTGCTCCGGG AAAGCAGAAG TTCTTAATTA AGGAATTCCT TGCATGTCTG CCGAATTTTC GGAAATTTTT
```

FIG. 6H

```
                                                                                              apoI
4321  CGTTTTTAAG GGGTTTGTAG ACAAGGTAAA GGATAAAACA GCACAATTCC AAGAAAAACA CGATTAGAAA CCTAAAAAGA ACGAATTTGA ACTAACTCAT
      GCAAAAATTC CCCAAACATC TGTTCCATTT CCTATTTTGT CGTGTTAAGG TTCTTTTTGT GCTAAATCTT GGATTTTTCT TGCTTAAACT TGATTGAGTA
              accI
                                                                                                                xmnI
                                                                                                                asp700
4421  AACCGAGAGG TAAAAAAAGA ACGAAGTCGA GATCAGGGAA TGAGTTTATA AAATAAAAAA AGCACCTGAA AAGGTGTCTT TTTTTGATGG TTTTGAACTT
      TTGGCTCTCC ATTTTTTTCT TGCTTCAGCT CTAGTCCCTT ACTCAAATAT TTTATTTTTT TCGTGGACTT TTCCACAGAA AAAAACTACC AAAACTTGAA
                                                                                                         ahaIII/draI
4521  GTTCTTTCTT ATCTTGATAC ATATAGAAAT AACGTCATTT TTATTTTAGT TGCTGAAAGG TGCCGTTGAAG TGTTGGTATG TATGTGTTTT AAAGTATTGA
      CAAGAAAGAA TAGAACTATG TATATCTTTA TTGCAGTAAA AATAAAATCA ACGACTTTCC ACGCAACTTC ACAACCATAC ATACACAAAA TTTCATAACT
                                                                                                        sspI
4621  AAACCCCTTAA AATTGGTTGC ACAGAAAAAC CCCATCTGTT AAAGTTATAA GTGACTAAAC AAATAACTAA TTTATTGATT CACTGATTTG TATCTACCCC CAAAGAAAAT TATAATACAC
      TTTGGGAATT TTAACCAACG TGTCTTTTTG GGGTAGACAA TTTCAATATT CACTGATTTG GTTGACTAAAC
                                                             styI
                                                             ncoI
                                                             bsaI dsaI
4721  TCCTAATAGT AGCATTTATT CAGATGAAAA ATCAAGGGTT TTAGTGGACA AGACAAAAAG TGGAAAAGTG AGACCATGGA GAGAAAAGAA AATCGCTAAT
      AGGATTATCA TCGTAAATAA GTCTACTTTT TAGTTCCCAA AATCACCTGT TCTGTTTTTC ACCTTTTCAC TCTGGTACCT CTCTTTTCTT TTAGCGATTA
                 ahaIII/draI
                 apoI                                                                  sspI
4821  GTTGATTACT TTGAACTTCT GCATATTCTT GAATTTAAAA AGGCTGAAAG CTTAAATTTT TCCGACTTTC ATAATCTCAT ATTTGTTTTA GCACTTTGTC
      CAACTAATGA AACTTGAAGA CGTATAAGAA CTTAAATTTT TCCGACTTTT GAATTTAAAA AGGCTGAAAG
              xcmI      gsuI/bpmI                                                          bsmI
4921  GCGAAAGAAA GTTGTATCGA GTGTGGTTTT GTAAATCCAG GCTTTGTCCA ATGTGCAACT GGAGGAGAGC CCTCCTCCG TTACTTTGTA GGCATTCAGT CACAAAAGGT
      CGCTTTCTTT CAACATAGCT CACACCAAAA CATTTAGGTC CGAAACAGGT TACACGTTGA CCTCCTCCG TTACTTTGTA CCGTAAGTCA GTGTTTTCCA
```

FIG. 6I

```
                 eco57I
5021  TGTTGCTGAA GTTATTAAAC AAAAGCCAAC AGTTCGTTGG TTGTTTCTCA CATTAACAGT TAAAAATGTT TATGATGGCG AAGAATTAAA TAAGAGTTTG
      ACAACGACTT CAATAATTTG TTTTCGGTTG TCAAGCAACC AACAAAGAGT GTAATTGTCA ATTTTACAA ATACTACCGC TTCTTAATTT ATTCTCAAAC xcmI
                                                              aseI/asnI/vspI
5121  TCAGATATGG CTCAAGGATT TCGCCGAATG ATGCAATATA AAAAAATTAA TAAAAATCTT GTTGGTTTTA TGCGTGCAAC GGAAGTGACA ATAAATAATA
      AGTCTATACC GAGTTCCTAA AGCGGCTTAC TACGTTATAT TTTTTTAATT ATTTTTAGAA CAACCAAAAT ACGCACGTTG CCTTCACTGT TATTTATTAT nspI
                                     nspHI
                                     ppu10I
                                     nsiI/avaIII
                                     nspI
                                     nspHI                        bsaAI
5221  AAGATAATTC TTATAATCAG CACATGCATG TATTGGTATG TGTGGAACCA ACTTATTTTA AGAATACAGA AAACTACGTG AATCAAAAAC AATGGATTCA
      TTCTATTAAG AATATTAGTC GTGTACGTAC ATAACCATAC ACACCTTGGT TGAATAAAAT TCTTATGTCT TTTGATGCAC TTAGTTTTTG TTACCTAAGT munI
                                                                    mcrI
5321  ATTTTGGAAA AAGGCAATGA AATTAGACTA TGATCCAAAT TTAATCTGAT ACTAGGTTTA ACCGAAAAAT AAATATAAAT CGGATATACA ATCGGCAATT
      TAAAACCTTT TTCCGTTACT TTAATCTGAT ACTAGGTTTA TGATCCAAAT TGGCTTTTTA TTTATATTTA GCCTATATGT TAGCCGTTAA apoI  pspI406I
5421  GACGAAACTG CAAAATATCC TGTAAAGGAT ACGGATTTTA TGAAGAAAAG AATTTGAAAC GTTTGTCTGA TTTGGAGGAA GGTTACACC
      CTGCTTTGAC GTTTTATAGG ACATTTCCTA TGCCTAAAAT ACTTCTTTTC TTAAACTTTG CAAACAGACT AAACCTCCTT CCAAATGTGG 5521  GTAAAAGGTT AATCTCCTAT GGTGGTTTGT TAAAAGAAAT ACATAAAAAA TTAAACCTTG ATGACACAGA AGAAGGCGAT TTGATTCATA CAGATGATGA
      CATTTTCCAA TTAGAGGATA CCACCAAACA ATTTTCTTTA TGTATTTTTT AATTTGGAAC TACTGTGTCT TCTTCCGCTA AACTAAGTAT GTCTACTACT 5621  CGAAAAAGCC GATGAAGATG GATTTTCTAT TATTGCAATG TGGAATTGGG AACGGAAAAA TTATTTTATT AAAGAGTAGT TCAACAAACG GGCCAGTTTG
      GCTTTTTCGG CTACTTCTAC CTAAAAGATA ATAACGTTAC ACCTTAACCC TTGCCTTTTT AATAAAATAA TTTCTCATCA AGTTGTTTGC CCGGTCAAAC
```

FIG. 6J

```
                                                             hgiAI/aspHI
                                                             bsp1286
                                                             bsiHKAI
                     bpuAI            aseI/asnI/vspI         bmyI          sspI
                     bbsI                                                              rcaI
                                                                                       bspHI
5721 TTGAAGATTA GATGCTATAA TTGTTATTAA AAGGATTGAA GGATGCTTAG GAAGACGAGT TGAATAAGAA CGGTGCTCTC CAAATATTCT
     AACTTCTAAT CTACGATATT AACAATAATT TTCCTAACTT CCTACGAATC CTTCTGCTCA ATAATTATCG ACTTATTCTT GCCACGAGAG GTTTATAAGA 5821 TATTTAGAAA AGCAAATCTA AAATTATCTG AAAAGGGAAT GAGAATAGTG AATGGACCAA TAATAATGAC TAGAGAAGAA AGAATGAAGA TTGTTCATGA
     ATAAATCTTT TCGTTTAGAT TTTAATAGAC TTTTCCCTTA CTCTTATCAC TTACCTGGTT ATTATTACTG ATCTCTTCTT TCTTACTTCT AACAAGTACT hgiJII
                                                                           ecoO109I/draII
                                                                           bsp1286
                                                                           bsp120I
                                                                           bmyI
                                                                           banII
                                                                           apaI
5921 AATTAAGGAA CGAATATTGG ATAAATATGG GGATGATGTT AAGGCTATTG GTGTTTATGG CTCTCTTGGT CGTCAGACTG ATGGGCCCTA TTCGGATATT
     TTAATTCCTT GCTTATAACC TATTTATACC CCTACTACAA TTCCGATAAC CACAAATACC GAGAGAACCA GCAGTCTGAC TACCCGGGAT AAGCCTATAA
              sspI
                                                cfr10I                                                xmnI
                                                bsaWI                                                 earI/ksp632I
                              hincII/hindII     ageI                                         apoI     asp700
6021 GAGATGATGT GTGTCATGTC AACAGAGGAA GCAGAGTTCA GCCATGAATG GACAACCGGT GAGTGGAAGG TGGAAGTGAA TTTTGATAGC GAAGAGATTC
     CTCTACTACA CACAGTACAG TTGTCTCCTT CGTCTCAAGT CGGTACTTAC CTGTTGGCCA CTCACCTTCC ACCTTCACTT AAAACTATCG CTTCTCTAAG ppu10I        eaeI
              nsiI/avaIII   cfrI
6121 TACTAGATTA TGCATCTCAG ACGTAGAGTC ATTGGCCGCT TACACATGGT CAATTTTTCT CTATTTTGCC GATTTATGAT TCAGGTGGAT ACTTAGAGAA
     ATGATCTAAT ACGTAGAGTC TGCATCTCAG TAACCGGCGA ATGTGTACCA GTTAAAAAGA GATAAAACGG CTAAATACTA AGTCCACCTA TGAATCTCTT
```

FIG. 6K

```
                                        bsp1286            sapI
                            psp1406I     bmyI           earI/ksp632I
6221 AGTGTATCAA ACTGCTAAAT CGGTAGAAGC CACGATGCGA TTTGTGCCCT TATCGTAGAA GAGCTGTTG AATATGCAAG CAAATGGCGT
     TCACATAGTT TGACGATTTA GCCATCTTCG GTGCTACGCT AAACACGGGA ATAGCATCTT CTCGACAAAC TTATACGTCC GTTTACCGCA sspI                                                           hgICI
                                                                    banI
6321 AATATTCGTG TGCAAGGACC GACAACATTT CTACCATCCT TGACTGTACA GGTAGCAATG GCAGGTGCCA TGTTGATTGG TCTGCATCAT CGCATCTGTT
     TTATAAGCAC ACGTTCCTGG CTGTTGTAAA GATGGTAGGA ACTGACATGT CCATCGTTAC CGTCCACGGT ACAACTAACC AGACGTAGTA GCGTAGACAA haeII                        bsp1407I              bspMI
        eco47III                     bstYI/xhoII                                        hincII/hindII
6421 ATACGACGAG CGCTTCGGTC TTAACTGAAG ATCAGATCTT CCTTCAGGTT ATGACCATCT GTGCCAGTTC GTAATGTCTG GTCAACTTTC
     TATGCTGCTC GCGAAGCCAG AATTGACTTC GTCTCTAGAA GGAAGTCCAA TACTGGTAGA CACGGTCAAG CATTACAGAC CAGTTGAAAG apoI
6521 CGACTCTGAG AAACTTCTGG AATGCGCTAGA GAATTTCTGG AATGGGATTC AGGAGTGGAC AGAACGACAC GGATATATAG TGGATGTGTC AAAACGCATA
     GCTGAGACTC TTTGAAGACC TTACGCGATCT CTTAAAGACC TTACCCTAAG TCCTCACCTG TCTTGCTGTG CCTATATATC ACCTACACAG TTTTGCGTAT snaBI
                                              bsaAI                                           aseI/asnI/vspI
6621 CCATTTTGAA CGATGACCTC TAATAATTGT GGTTACGTAT TTATTAACTT CTCCTAGTAT TAGTAATTAT CATGGCTGTC ATGGCGCATT
     GGTAAAACTT GCTACTGGAG ATTATTAACA CCAATGCATA AATAATTGAA GAGGATCATA ATCATTAATA GTACCGACAG TACCGCGTAA aseI/asnI/vspI
6721 AACGGAATAA AGGGTGTGCT CATTTTGCGT TAAATCGGGC AATAAGAAAA AGGATTAATT ATGAGCGAAT TGAATTAATA ATAAGGTAAT AGATTTACAT
     TTGCCTTATT TCCCACACGA GTAAAACGCA ATTTAGCCCG TTATTCTTTT TCCTAATTAA TACTCGCTTA ACTTAATTAT TATTCCATTA TCTAAATGTA 6821 TAGAAAATGA AAGGGGATTT TATGCGTGAG AATGTTACAG TCTATCCCGG CAATAGTTAC CCTTATTATC AAGATAAGAA AGAAAAGGAT TTTTCGCTAC
     ATCTTTTACT TTCCCCTAAA ATACGCACTC TTACAATGTC AGATAGGGCC GTTATCAATG GGAATAATAG TTCTATTCTT TCTTTTCCTA AAAAGGCATG
```

FIG. 6L

```
                    ahaII/draI
6921  GCTCAAATCC TTTAAAAAAA CACAAAAGAC CACATTTTTT AATGTGGTCT TTATTCTTCA ACTAAAGCAC CCATTAGTTC AACAAACGAA AATTGGATAA
      CGAGTTTAGG AAATTTTTTT GTGTTTTCTG GTGTAAAAAA TTACACCAGA AATAAGAAGT TGATTCGTG GGTAATCAAG TTGTTTGCTT TTAACCTATT ahaII/draI                       sspI                                                            apoI
7021  AGTGGGATAT TTTTAAAATA TATATTTATG TTACAGTAAT ATTGACTTTT AAAAAAGGAT TGATTCTAAT GAAGAAAGCA GACAAGTAAG CCTCCTAAAT
      TCACCCTATA AAAATTTTAT ATATAAATAC AATGTCATTA TAACTGAAAA TTTTTTCCTA ACTAAGATTA CTTCTTTCGT CTGTTCATTC GGAGGATTTA apoI                                                          munI    earI/ksp632I
7121  TCACTTTAGA TAAAAATTTA GGAGGCATAT CAAATGAACT TTAATAAAAT TGATTTAGAC AATTGGAAGA GAAAAGAGAT ATTTAATCAT TATTTGAACC
      AGTGAAATCT ATTTTTAAAT CCTCCGTATA GTTTACTTGA AATTATTTTA ACTAAATCTG TTAACCTTCT CTTTTCTCTA TAAATTAGTA ATAAACTTGG apoI
7221  AACAAACGAC TTTTAGTATA ACCACAGAAA TTGATATTAG TCTTTTATAC CGAAACATAA AACAAGAAGG ATATAAATTT TACCCTGCAT TTATTTTCTT
      TTGTTTGCTG AAAATCATAT TGGTGTCTTT AACTATAATC ACAAAATATG GCTTTGTATT TTGTTCTTCC TATATTTAAA ATGGGACGTA AATAAAAGAA 7321  AGTGACAAGG GTGATAAACT CAAATACAGC TTTTAGAAAT GGTTACAATA GCGACGGAGA GTTAGGTTAT TGGGATAAGT TAGAGCCACT TTATACAATT
      TCACTGTTCC CACTATTTGA GTTTATGTCG AAAATCTTGA CCAATGTTAT CGCTGCCTCT CAATCCAATA ACCCTATTCA ATCTCGGTGA AATATGTTAA xmnI
                          asp700                                                       styI
                                                                                       ncoI
7421  TTTGATGGTG TATCTAAAAC ATTCTCTGGT ATTTGGACTC CTGTAAAGAA TGACTTCAAA GAGTTTTATG ATTTATACCT TTCTGATGTA GAGAAATATA
      AAACTACCAC ATAGATTTTG TAAGAGACCA TAAACCTGAG GACATTTCTT ACTGAAGTTT CTCAAAATAC TAAATATGGA AAGACTACAT CTCTTTATAT dsaI
7521  ATGGTTCGGG GAAATTGTTT CCCAAAACAC CTATACCTGA AAATGCTTTT TCTCTTTCTA TTATTCCATG GACTTCATTT ACTGGGTTTA ACTTAAATAT
      TACCAAGCCC CTTTAACAAA GGGTTTTGTG GATATGGACT TTTACGAAAA AGAGAAAGAT AATAAGGTAC CTGAAGTAAA TGACCCAAAT TGAATTTATA apoI  aseI/asnI/vspI
7621  CAATAATAAT AGTAATTACC TTCTACCCAT TATTACAGCA GGAAATTCA TAATAAAGG TAATTCAATA TATTTACCGC TATCTTTACA GGTACATCAT
      GTTATTATTA TCATTAATGG AAGATGGGTA ATAATGTCGT CCTTTAAGT ATTATTTCC ATTAAGTTAT ATAAATGGCG ATAGAAATGT CCATGTAGTA

FIG. 6M
```

```
                                                          stuI
                                                          haeI
         mamI
         bsaBI
7721 TCTGTTTGTG ATGGTTATCA TGCAGGATTG TTTATGAACT CTATTCAAGA ATTGTCAGAT AGGCCTAATG ACTGGCTTTT ATAATATGAG ATAATGCCGA
     AGACAAACAC TACCAATAGT ACGTCCTAAC AAATACTTGA GATAAGTCCT TAACAGTCTA TCCGGATTAC TGACCGAAAA TATTATACTC TATTACGGCT mamI(dam-)
                                                                                  bsaBI(dam-)
                                                                                  bstYI/xhoII
                           bspMI                                                  gsuI/bpmI
7821 CTGTACTTTT TACAGTCGGT TTTCTAATGT CACTAACCTG CCCCGTTAGT TGAAGAAGGT TTTTATATTA CAGCTCCAGA TCCATATCCT TCTTTTTCTG
     GACATGAAAA ATGTCAGCCA AAAGATTACA GTGATTGGAC GGGGCAATCA ACTTCTTCCA AAAATATAAT GTCGAGGTCT AGGTATAGGA AGAAAAAGAC munI
7921 AACCGACTTC TCCTTTTTCG CTTCTTTATT CCAATTGCTT TATTGACGTT GAGCCTCGGA ACCCXTATAG TGTGTTATAC TTTACTTGGA AGTGGTTGCC
     TTGGCTGAAG AGGAAAAAGC GAAGAAATAA GGTTAACGAA ATAACTGCAA CTCGGAGCCT TGGG?ATATC ACACAATATG AAATGAACCT TCACCAACGG ndeI                                       bsmI
8021 GGAAAGAGCG AAAATGCCTC ACATTTGTGC CACCTAAAAA GGAGCGGATTT ACATATGAGT TATGCAGTTT GTAGAATGCA AAAAGTGAAA TCAGGATCX
     CCTTTCTCGC TTTTACGGAG TGTAAACACG GTGGATTTTT CCTCGCTAAA TGTATACTCA ATACGTCAAA CATCTTACCT TTTTCACTTT AGTCCTAG?
```

SUBTILISIN VARIANTS CAPABLE OF CLEAVING SUBSTRATES CONTAINING DIBASIC RESIDUES

FIELD OF THE INVENTION

This invention relates to subtilisin variants having altered specificity from wild-type subtilisin useful for processing fusion proteins, especially those made in recombinant cell culture. Specifically, the subtilisin variants are modified so that they efficiently and selectively cleave substrates containing dibasic residues.

BACKGROUND OF THE INVENTION

Site-specific proteolysis is one of the most common forms of post-translational modifications of proteins (for review see Neurath, H. |1989| Trends Biochem. Sci., 14:268). In addition, proteolysis of fusion proteins in vitro is an important research and commercial tool (for reviews see Uhlen, M. and Moks, T. |1990| Methods Enzymol., 185:129-143; Carter, P. |1990| in Protein Purification: From Molecular Mechanisms to Large-Scale Processes, M. R. Landisch, R. C. Wilson, C. D. Painton, S. E. Builder, Eds. |ACS Symposium Series 427, American Chemical Society, Washington, D.C.|, Chap. 13, p.181–193; and Nilsson, B. et al. |1992| Current Opin. Struct. Biol., 2:569). Expressing a protein of interest as a fusion protein facilitates purification when the fusion contains an affinity domain such as glutathione-S-transferase, Protein A or a poly-histidine tail. The fusion domain can also facilitate high level expression and/or secretion.

To liberate the protein product from the fusion domain requires selective and efficient cleavage of the fusion protein. Both chemical and enzymatic methods have been proposed (see references above). Enzymatic methods are generally preferred as they tend to be more specific and can be performed under mild conditions that avoid denaturation or unwanted chemical side-reactions. A number of natural and even designed enzymes have been applied for site-specific proteolysis. Although some are generally more useful than others (Forsberg, G., Baastrup, B., Rondahl, H., Holmgren, E., Pohl, G., Hartmanis, M. and Lake, M. |1992| J. Prot. Chem., 11:201–211), no one is applicable to every situation given the sequence requirements of the fusion protein junction and the possible existence of protease sequences within the desired protein product. Thus, an expanded array of sequence specific proteases, analogous to restriction endonucleases, would make site-specific proteolysis a more widely used method for processing fusion proteins or generating protein/peptide fragments either in vitro or in vivo.

One of the most popular site-specific proteolysis events is the maturation of pro-hormones by the KEX2-family of enzymes that are present in eukaryotic cells (for reviews see Steiner, D. F., Smeekens, S. P., Ohagi, S. and Chan, S. J. |1992| J. Biol. Chem., 267:23435–23438 and Smeekens, S. P. |1993| Bio/Technology, 11:182–186). This family of proteases, that includes the yeast KEX2 and the mammalian PC2 and furin enzymes, are homologous to the bacterial serine protease subtilisin (Kraut, J. |1977| Annu. Rev. Biochem. . . . , 46:331–358). Subtilisin has a broad substrate specificity that reflects its role as a scavenger protease. In contrast, these eukaryotic enzymes are very specific for cleaving substrates containing two basic residues and thus well-suited for site-specific proteolysis. However, the eukaryotic proteases are expressed in small amounts (Bravo, D. B., Gleason, J. B., Sanchez, R. I., Roth, R. A., and Fuller, R. S. |1994| J. Biol. Chem., 269:25830–25837 and Matthews, D. J., Goodman, L. J., Gorman, C. M., and Wells, J. A. |1994| Protein Science, 3:1197–1205) making them impractical to apply presently to processing of fusion proteins in vitro.

Despite the very narrow specificity of the pro-hormone processing enzymes, in some cases they are capable of rapid cleavage of target sequences. For example, the $k_{cat}/Km$ ratio for KEX2 to cleave a good substrate (e.g. Boc-RVRR-MCA) is $1 \times 10^6 \, M^{-1} s^{-1}$ (Brenner, C., and Fuller, R. S. |1992| Proc. Natl. Acad. Sci. USA, 89:922–926) compared to $3 \times 10^5$ for subtilisin cleaving a good substrate (e.g. suc-AAPF-pna) (Estell, D. A., Graycar, T. P., Miller, J. V., Powers, D. B., Burnier, J. P., Ng, P. G. and Wells, J. A. |1986| Science, 233:659–663). Given the fact that subtilisin BPN' can be expressed in large amounts (Wells, J. A., Ferrari, E., Henner, D. J., Estell, D. A. and Chen, E. Y. |1983| Nucl. Acids Res., 11:7911–7929) we wondered if it would be possible to engineer the specificity of subtilisin to be like that of KEX2, to produce a useful subtilisin variant for processing fusion proteins or generating protein fragments by cleavage at designed dibasic sites.

Previous attempts to introduce or reverse charge specificity in enzyme active sites have been met with considerable difficulty. This has generally been attributed to a lack of stabilization of the introduced charge or enzyme-substrate ion pair complex by the wild-type enzyme environment (Hwang, J. K. and Warshel, A. |1988| Nature, 334:270–272). For example, Stennicke et. al (Stennicke, H. R.; Ujje, H. M.; Christensen, U.; Remington, S. J.; and Breddam |1994| Prot. Eng. 7:911–916) made acidic (D/E) mutations at five residues in the P1' binding of carboxypeptidase Y in an attempt to change the P1' preference from Phe to Lys/Arg. Only the L272D and L272E mutations were found to alter the specificity in the desired direction, up to 1.5-fold preference in Lys/Arg over Phe, and the others simply resulted in less active enzymes having substrate preferences similar to wild-type. In the case of trypsin, a protease that is highly specific for basic P1 residues, recruitment of chymotrypsin-like (hydrophobic P1) specificity required not only mutations of the ion pair-forming Asp 189 to Ser, but also transplantation of two more distant surface loops from chymotrypsin (Graf, L., Jancso, A., Szilagyi, L., Hegyi, G., Pinter, K., Naray-Szabo, G., Hepp, J., Medzihradszky, K., and Rutter, W. J., Proc. Natl. Acad. Sci. USA |1988| 85:4961–4965 and Hedstrom, L., Szilagyi, L., and Rutter, W. J., Science |1992| 255:1249–1253).

In the present work, we have also verified that relatively low specificity is gained by introducing single ion-pairs between enzyme and substrate. However, when two choice ionic interactions were simultaneously engineered into subtilisin BPN', the resulting variant had higher specificity for basic residues in each of the subsites due to a non additive effect.

Accordingly, it is an object to produce a subtilisin variant with dibasic specificity for use in processing pro-proteins made by recombinant techniques.

SUMMARY OF THE INVENTION

The invention includes subtilisin variants, having a substrate specificity which is substantially different from the substrate specificity of the precursor subtilisin from which the amino acid sequence of the mutant is derived. The substrate specificity of the preferred subtilisin variants is for substrates having dibasic amino acid residues. The preferred precursor subtilisin is subtilisin from Bacillus

*amyloliquefaciens*, referred to as subtilisin BPN'. The amino acid sequence of the subtilisin variants are derived by the substitution of one or more amino acids of the precursor subtilisin amino acid sequence. The preferred subtilisin variants having substrate specificity for dibasic substrates have a different amino acid residue at residue position +62 than subtilisin naturally produced by *Bacillus amyloliquefaciens*. The naturally occurring Asn (N) at residue position +62 of subtilisin BPN' is preferably substituted with an acidic amino acid residue such as Glu (E) or Asp (D), most preferably D. The most preferred subtilisin variants, having substrate specificity for substrates having dibasic amino acid residues, additionally have an acidic residue, E or D, at residue position +62 of subtilisin BPN'. Thus the subtilisin BPN' variant N62D/G166D may be used to cleave fusion proteins with dibasic substrate linkers and processing hormones or other proteins (in vitro or in vivo) that contain dibasic cleavage sites.

Preferred substrates for the subtilisin BPN' variant N62D/G166D contain either Lys (K) or Arg (R) at substrate positions P2 and P1, practically any residue at P3, a non-charged hydrophobic residue at P4, and again practically any residue at P5. Thus an exemplary good substrate would contain -Asn-Leu-Met-Arg-Lys- (SEQ ID NO: 35) at -P5-P4-P3-P2-P1- respectively. Additionally, good substrates would not have Pro at P1', P2', or P3' nor would Ile be present at P1'. Thus the invention includes a process comprising contacting the subtilisin variant having substrate specificity for dibasic amino acid residues with a substrate containing the above described amino acid residues under conditions.

The invention also includes mutant DNA sequences encoding such subtilisin variants. These mutant DNA sequences are derived from a precursor DNA sequence which encodes a naturally occurring or recombinant precursor subtilisin. The mutant DNA sequence is derived by modifying the precursor DNA sequence to encode the substitution(s) of one or more amino acids encoded by the precursor DNA sequence. These recombinant DNA sequences encode mutants having an amino acid sequence which does not exist in nature and a substrate specificity which is substantially different from the substrate specificity of the precursor subtilisin encoded by the precursor DNA sequence.

Further the invention includes expression vectors containing such mutant DNA sequences as well as host cells transformed with such vectors which are capable of expressing the subtilisin variants.

BRIEF DESCRIPTION OF THE FIGURES

Figure 6A:
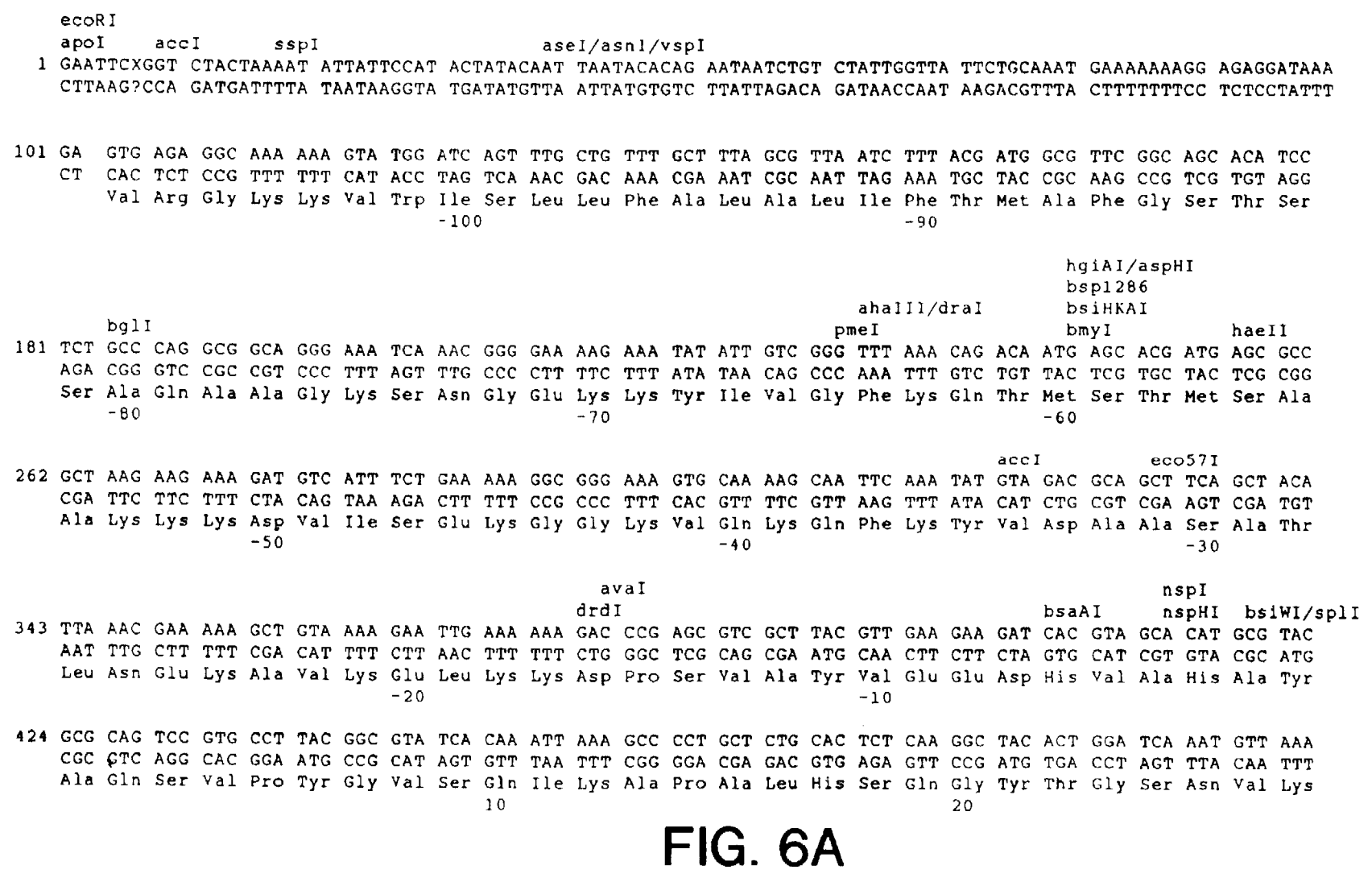

FIG. 6A–6N. (Collectively referred to herein as FIG. 6). DNA sequence of the phagemid pSS5 containing the N62D/G166D double mutant subtilisin BPN' gene (SEQ ID NO: 1), and translated amino acid sequence for the mutant prepro-subtilisin (SEQ ID NO: 2). The pre region is comprised of residues −102 to −76, the pro of residues −75 to −1, and the mature enzyme of residues +1 to +275 (SEQ ID NO: 72). Also shown are restriction sites recognized by endonucleases that require 6 or more specific bases in succession.

DETAILED DESCRIPTION OF THE INVENTION

Definitions

Figure 1:
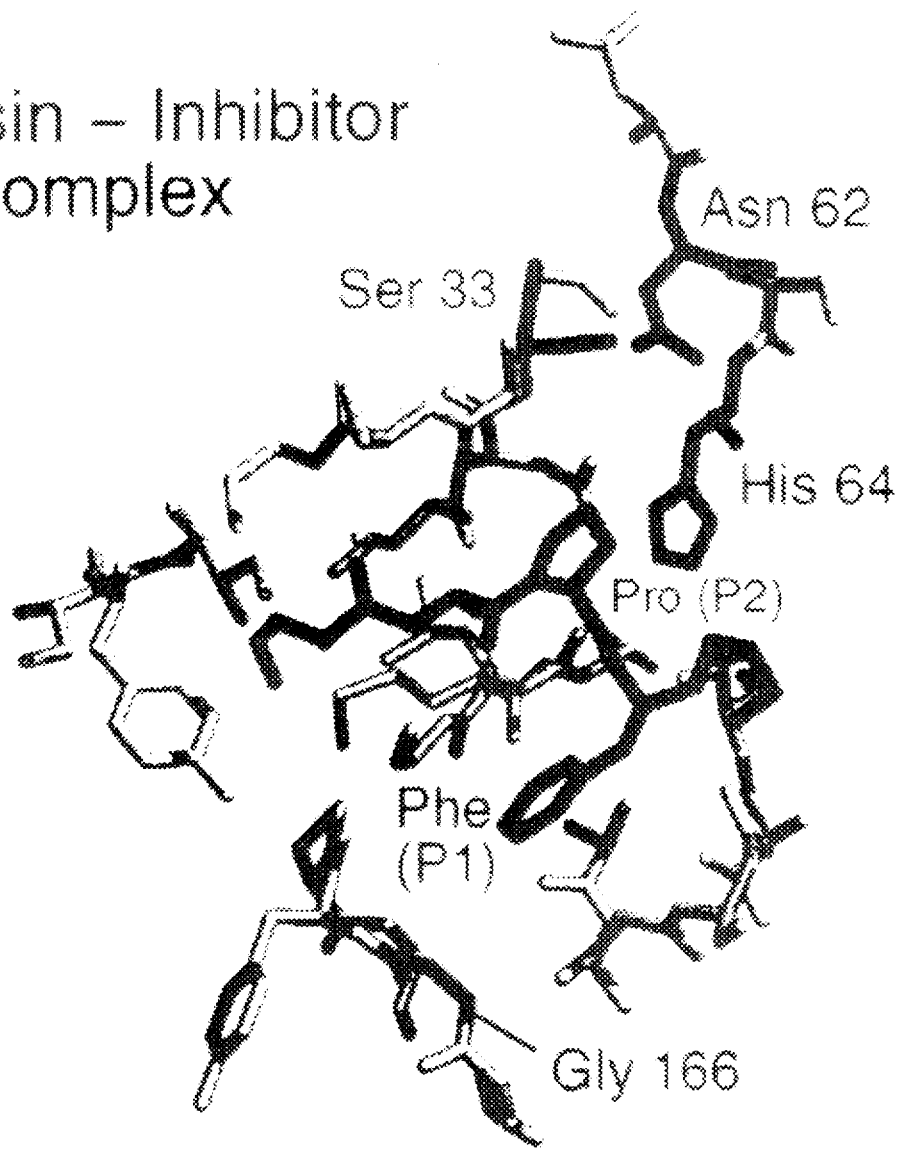
FIG. 1. Structure of a succinyl-Ala-Ala-Pro-BoroPhe (SEQ ID NO: 69) inhibitor bound to the active site of subtilisin BPN' showing the S2 and S1 binding pocket residues subjected to mutagenesis.

Terms used in the claims and specification are defined as set forth below unless otherwise specified.

The term amino acid or amino acid residue, as used herein, refers to naturally-occurring L α-amino acids or residues, unless otherwise specifically indicated. The commonly used one- and three-letter abbreviations for amino acids are use herein (Lehninger, A. L., *Biochemistry*, 2d ed., pp. 71–92, Worth Publishers, N.Y. [1975]).

Substrates are described in triplet or single letter code as Pn . . . P2-P1-P1'-P2'. . . Pn'. The "P$_1$" residue refers to the position proceeding the scissile peptide bond (i.e. between the P1 and P1' residues) of the substrate as defined by Schechter and Berger (Schechter, I. and Berger, A., *Biochem. Biophys. Res. Commun.* 27: 157–162 [1967]).

"Subtilisins" are bacterial carbonyl hydrolases which generally act to cleave peptide bonds of proteins or peptides. As used herein, "subtilisin" means a naturally occurring subtilisin or a recombinant subtilisin. A series of naturally occurring subtilisins are known to be produced and often secreted by various bacterial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus is aspartate-histidine-serine. In the chymotrypsin related proteases the relative order, however is histidine-aspartate-serine. Thus, subtilisins as used herein refer to a serine protease having the catalytic triad of subtilisin related proteases.

Generally, subtilisins are serine endoproteases' having molecular weights of about 27,500 which are secreted in large amounts from a wide variety of Bacillus species. The protein sequence of subtilisins have been determined from at least four different species of Bacillus. Markland, F. S., et al. (1971) in *The Enzymes*, ed. Boyer P. D., Acad Press, New York, Vol. III, pp. 561–608 and Nedkov, P. et al. (1983) *Hoppe-Seyler's Z. Physiol. Chem.* 364:1537–1540. The three-dimensional crystallographic structure of subtilisin BPN' (from *B. amyloliquefaciens*) to 2.5A_ resolution has also been reported by Wright, C. S. et al. |1969| *Nature* 221:235–242 and Drenth, J. et al. |1972| *Eur. J. Biochem.* 26:177–181. These studies indicate that although subtilisin is genetically unrelated to the mammalian serine proteases, it has a similar active site structure. The x-ray crystal structures of subtilisin containing covalently bound peptide inhibitors (Robertus, J. D., et al. |1972| *Biochemistry* 11:2439–2449), product complexes (Robertus, J. D., et al. |1972| *Biochemistry* 11:4293–4303), and transition state analogs (Matthews, D. A., et al. |1975| *J. Biol. Chem.* 250:7120–7126 and Poulos, T. L., et al. |1976| *J. Biol. Chem.* 251:1097–1103), which have been reported have also provided information regarding the active site and putative substrate binding cleft of subtilisins. In addition, a large number of kinetic and chemical modification studies have been reported for subtilisins (Phillip, M., et al. |1983| *Mol. Cell. Biochem.* 51:5–32; Svendsen, I. B. |1976| *Carlsberg Res. Comm.* 41:237–291 and Markland, F. S. Id.) as well as at least one report wherein the side chain of methione at residue 222 of subtilisin was converted by hydrogen peroxide to methionine-sulfoxide (Stauffer, D. C., et al. |1965| *J. Biol. Chem.* 244:5333–5338).

"Recombinant subtilisin" refers to a subtilisin in which the DNA sequence encoding the subtilisin is modified to produce a mutant DNA sequence which encodes the substitution of one or more amino acids in the naturally occurring subtilisin amino acid sequence. Suitable methods to produce such modification include those disclosed in U. S. Pat. Nos. 4,760,025 and 5,371,008 and in EPO Publication No. 0130756 and 0251446.

When referring to mutants or variants, the wild type amino acid residue is 30 followed by the residue number and the new or substituted amino acid residue. For example, substitution of D for wild type N in residue position 62 is denominated N62D.

"Subtilisin variants or mutants" are designated in the same manner by using the single letter amino acid code for the wild-type residue followed by its position and the single letter amino acid code of the replacement residue. Multiple mutants are indicated by component single mutants separated by slashes. Thus the subtilisin BPN' variant N62D/G166D is a di-substituted variant in which Asp replaces Asn and Gly at residue positions 62 and 166 in wild-type subtilisin BPN'.

Specific residues of *B. amyloliquefaciens* subtilisin are identified for substitution. These amino acid residue position numbers refer to those assigned to the *B. amyloliquefaciens* subtilisin sequence (SEQ ID NO: 74) see the mature sequence in FIG. 1. of U.S. Pat. No. 4,760,025). The invention, however, is not limited to the mutation of this particular subtilisin but extends to precursor carbonyl hydrolases containing amino acid residues which are "equivalent" to the particular identified residues in *B. amyloliquefaciens* subtilisin. An amino acid residue of a precursor carbonyl hydrolase is "equivalent" to a residue of *B. amyloliquefaciens* subtilisin if it is either homologous (i.e., corresponding in position in either primary or tertiary structure) or analogous to a specific residue or portion of that residue in *B. amyloliquefaciens* subtilisin (i.e., having the same or similar functional capacity to combine, react, or interact chemically).

Figure 5:
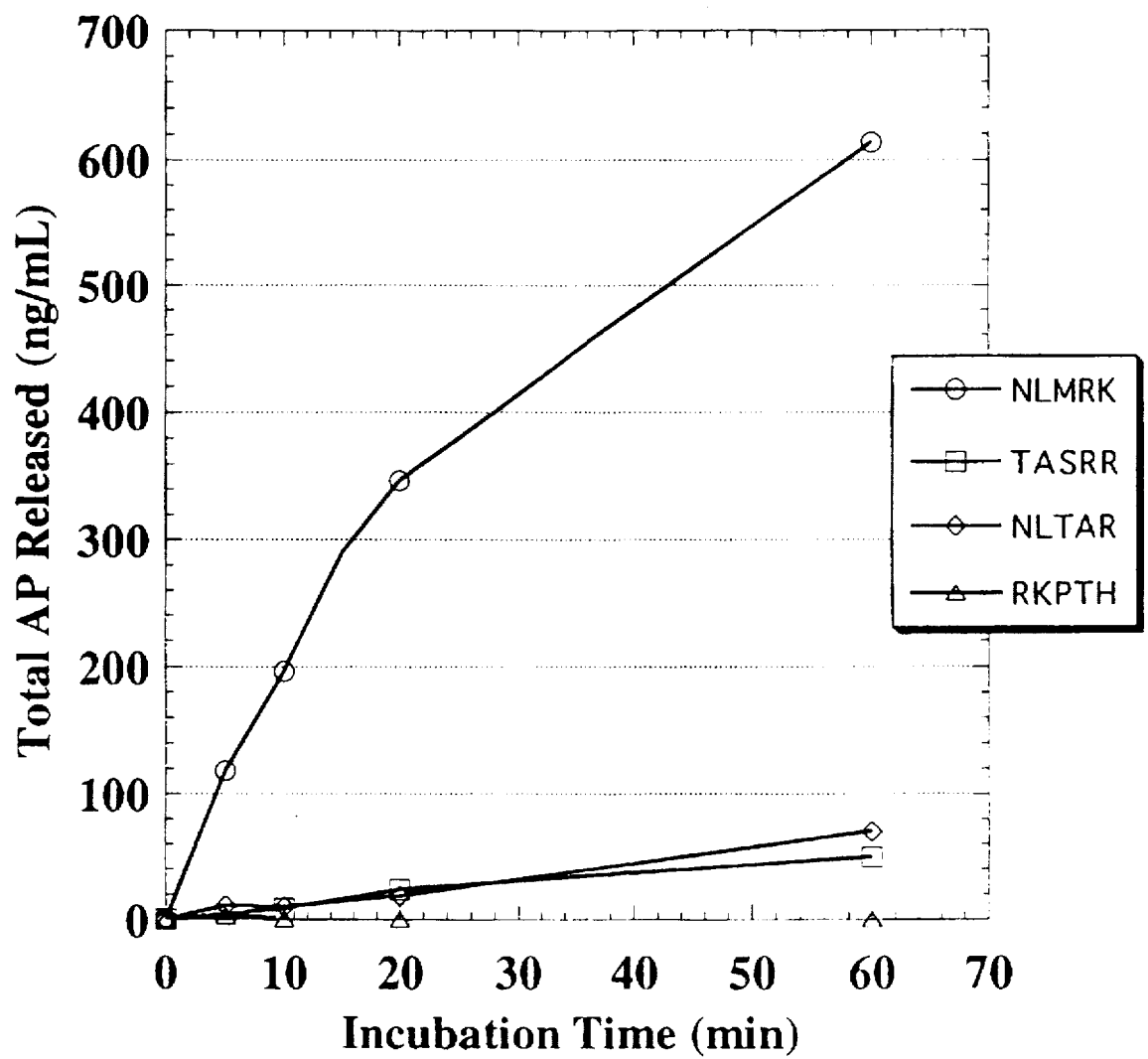
FIG. 5. Results of hGH-AP fusion protein assay. hGH-AP fusion proteins were constructed, bound to hGHbp-coupled resin, and treated with 0.5 nM N62D/G166D subtilisin in 20 mM Tris-Cl pH 8.2. Aliquots were withdrawn at various times and AP release was monitored by activity assay in comparison to a standard curve as described (10, 19).

In order to establish homology to primary structure, the amino acid sequence of a precursor carbonyl hydrolase is directly compared to the *B. amyloliquefaciens* subtilisin primary sequence and particularly to a set of residues known to be invariant in all subtilisins for which the sequences are known (see e.g. FIG. 5-C in EPO 0251446). After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *B. amyloliquefaciens* subtilisin are defined. Alignment of conserved residues should conserve 100% of such residues. However, alignment of greater than 75% or as little as 50% of conserved residues is also adequate to define equivalent residues. Conservation of the catalytic triad, Asp32/His64/Ser221, is required.

Equivalent residues homologous at the level of tertiary structure for a precursor carbonyl hydrolase whose tertiary structure has been determined by x-ray crystallography, are defined as those for which the atomic coordinates of 2 or more of the main chain atoms of a particular amino acid residue of the precursor carbonyl hydrolase and *B. amyloliquefaciens* subtilisin (N on N, CA on CA, C on C, and O on O) are within 0.13 nm and preferably 0.1 nm after alignment. Alignment is achieved after the best model has been oriented and positioned to give the maximum overlap of atomic coordinates of non-hydrogen protein atoms of the carbonyl hydrolase in question to the *B. amyloliquefaciens* subtilisin. The best model is the crystallographic model giving the lowest R factor for experimental diffraction data at the highest resolution available.

$$R \text{ factor} = \frac{\sum_h |Fo(h)| - |Fc(h)|}{\sum_h |Fo(h)|}$$

Equivalent residues which are functionally analogous to a specific residue of *B. amyloliquefaciens* subtilisin are defined as those amino acids of the precursor carbonyl hydrolases which may adopt a conformation such that they either alter, modify or contribute to protein structure, substrate binding or catalysis in a manner defined and attributed to a specific residue of the *B. amyloliquefaciens* subtilisin as described herein. Further, they are those residues of the precursor carbonyl hydrolase (for which a tertiary structure has been obtained by x-ray crystallography), which occupy an analogous position to the extent that although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *B. amyloliquefaciens* subtilisin. The three dimensional structures would be aligned as outlined above.

Some of the residues, identified for substitution are conserved residues whereas others are not. In the case of residues which are not conserved, the replacement of one or more amino acids is limited to substitutions which produce a mutant which has an amino acid sequence that does not correspond to one found in nature. In the case of conserved residues, such replacements should not result in a naturally occurring sequence. The subtilisin mutants of the present invention include the mature forms of subtilisin mutants as well as the pro- and prepro-forms of such subtilisin mutants. The prepro-forms are the preferred construction since this facilitates the expression, secretion and maturation of the subtilisin mutants.

"Prosequence" refers to a sequence of amino acids bound to the N-terminal portion of the mature form of a subtilisin which when removed results in the appearance of the "mature" form of the subtilisin. Many proteolytic enzymes are found in nature as translational proenzyme products and, in the absence of post-translational processing, are expressed in this fashion. The preferred prosequence for producing subtilisin mutants, specifically subtilisin BPN' mutants, is the putative prosequence of *B. amyloliquefaciens* subtilisin although other subtilisin prosequences may be used.

A "signal sequence" or "presequence" refers to any sequence of amino acids bound to the N-terminal portion of a subtilisin or to the N-terminal portion of a prosubtilisin which may participate in the secretion of the mature or pro forms of the subtilisin. This definition of signal sequence is a functional one, meant to include all those amino acid sequences, encoded by the N-terminal portion of the subtilisin gene or other secretable carbonyl hydrolases, which participate in the effectuation of the secretion of subtilisin or other carbonyl hydrolases under native conditions. The present invention utilizes such sequences to effect the secretion of the subtilisin mutants as defined herein.

A "prepro" form of a subtilisin mutant consists of the mature form of the subtilisin having a prosequence operably linked to the amino-terminus of the subtilisin and a "pre" or "signal" sequence operably linked to the amino terminus of the prosequence.

"Expression vector" refers to a DNA construct containing a DNA sequence which is operably linked to a suitable control sequence capable of effecting the expression of the DNA in a suitable host. Such control sequences include a promoter to effect transcription, an optional operator sequence to control such transcription, a sequence encoding suitable niRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in EPO Publication No. 0130756 or 0251446 or U.S. Pat. No. 5,371,008 to render them incapable of secreting enzymatically active endoprotease. A preferred host cell for expressing subtilisin is the Bacillus strain BG2036 which is deficient in enzymatically active neutral protease and alkaline protease (subtilisin). The construction of strain BG2036 is described in detail in EPO Publication No. 0130756 and further described by Yang, M. Y., et al. (1984) *J. Bacteriol.* 160:15–21. Such host cells are distinguishable from those disclosed in PCT Publication No. 03949 wherein enzymatically inactive mutants of intracellular proteases in *E. coli* are disclosed. Other host cells for expressing subtilisin include *Bacillus subtilis* var. I168 (EPO Publication No. 0130756).

Host cells are transformed or transfected with vectors constructed using recombinant DNA techniques. Such transformed host cells are capable of either replicating vectors encoding the subtilisin mutants or expressing the desired subtilisin mutant. In the case of vectors which encode the pre or prepro form of the subtilisin mutant, such mutants, when expressed, are typically secreted from the host cell into the host cell medium.

"Operably linked" when describing the relationship between two DNA regions simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor subtilisin may be obtained in accord with the general methods described in U.S. Pat. No. 4,760,025 or EPO Publication No. 0130756. As can be seen from the examples disclosed therein, the methods generally comprise synthesizing labeled probes having putative sequences encoding regions of the hydrolase of interest, preparing genomic libraries from organisms expressing the hydrolase, and screening the libraries for the gene of interest by hybridization to the probes. Positively hybridizing clones are then mapped and sequenced.

The cloned subtilisin is then used to transform a host cell in order to express the subtilisin. The subtilisin gene is then ligated into a high copy number plasmid. This plasmid replicates in hosts in the sense that it contains the well-known elements necessary for plasmid replication: a promoter operably linked to the gene in question (which may be supplied as the gene's own homologous promotor if it is recognized, i.e., transcribed, by the host), a transcription termination and polyadenylation region (necessary for stability of the mRNA transcribed by the host from the hydrolase gene in certain eucaryotic host cells) which is exogenous or is supplied by the endogenous terminator region of the subtilisin gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the subtilisin gene into host genome. This is facilitated by procaryotic and eucaryotic organisms which are particularly susceptible to homologous recombination.

Once the subtilisin gene has been cloned, a number of modifications are undertaken to enhance the use of the gene beyond synthesis of the naturally-occurring precursor subtilisin. Such modifications include the production of recombinant subtilisin as disclosed in U.S. Pat. No. 5,371,008 or EPO Publication No. 0130756 and the production of subtilisin mutants described herein.

Mutant Design and Preparation.

A number of structures have been solved of subtilisin with a variety of inhibitors and transition state analogs bound (Wright, C. S., Alden, R. A. and Kraut, J. [1969] *Nature*, 221:235–242; McPhalen, C.A. and James, N.G. [1988] *Biochemistry*, 27:6582–6598; Bode, W., Papamokos, E., Musil, D., Seemueller, U. and Fritz, M. [1986] *EMBO J.*, 5:813–818; and Bott, R., Ultsch, M., Kossiakoff, A., Graycar, T., Katz, B. and Power, S. [1988] *J. Biol. Chem.*, 263:7895–7906). One of these structures, FIG. 1 was used to locate residues that are in close proximity to side chains at the P1 and P2 positions from the substrate. Previous work had shown that replacement residues at positions 156 and 166 in the S1 binding site with various charged residues lead to improved specificity for complementary charged substrates (Wells, J. A., Powers, D. B., Bott, R. R., Graycar, T. P. and Estell, D. A. |1987a| Proc. Natl. Acad. Sci. USA, 84:1219–1223). Although longer range electrostatic effects of substrate specificity have been noted (Russell, A. J. and Fersht, A. R. |1987| Nature, 328:496–500) these were generally much smaller than local ones. Therefore it seemed reasonable that local differences in charge between subtilisin BPN' and the eukaryotic enzymes may account for the differences in specificity.

A detailed sequence alignment of 35 different subtilisins (Siezen, R. J., de Vos, W. M., Leunissen, A. M., and Dijkstra, B. W. |1991| Prot. Eng., 4:719–737) allowed us to identify differences between subtilisin BPN' and the eukaryotic processing enzymes, KEX2, furin and PC2. Within the S1 binding pocket there are a number of charged residues that appear in the pro-hormone processing enzymes and not in subtilisin BPN' (Table 1A).

TABLE 1A

| | S1 subsite | | |
|---|---|---|---|
| | 125–131[a] | 151–157 | 163–168 |
| Subtilisin BPN' | SLGGPSG (SEQ ID NO: 3) | AAAGNEG (SEQ ID NO: 4) | ST-VGYP (SEQ ID NO: 5) |
| Kex2 | SWGPADD (SEQ ID NO: 6) | FASGNGG (SEQ ID NO: 7) | CNYDGYT (SEQ ID NO: 8) |
| Furin | SWGPEDD (SEQ ID NO: 9) | WASGNGG (SEQ ID NO: 10) | CNCDGYT (SEQ ID NO: 11) |
| PC2 | SWGPADD (SEQ ID NO: 6) | WASGDGG (SEQ ID NO: 12) | CNCDGYA (SEQ ID NO: 13) |

[a]numbering according to subtilisin BPN' sequence

For example, the eukaryotic enzymes have two conserved Asp residues at 130 and 131 as well as an Asp at 165 that is preceded by insertion of a Tyr or Cys. However, in the region from 151–157, subtilisin BPN' contains a Glu and the eukaryotes a conserved Gly.

In the S2 binding site there were two notable differences in sequence (Table 1B).

TABLE 1B

| | S2 subsite | |
|---|---|---|
| | 30–35 | 60–64 |
| Subtilisin BPN' | VIDSGI (SEQ ID NO: 14) | DNNSH (SEQ ID NO: 15) |
| KEX2 | IVDDGL (SEQ ID NO: 16) | SDDYH (SEQ ID NO: 17) |
| Furin | ILDDGI (SEQ ID NO: 18) | NDNRH (SEQ ID NO: 19) |
| PC2 | IMDDGI (SEQ ID NO: 20) | WFNSH (SEQ ID NO: 21) |

Subtilisin contains a Ser at position 33 whereas the pro-hormone processing enzymes contain Asp. There is not as clear a consensus in the region of 60–64, but one notable difference is at position 62. This side chain points directly at the P2 side chain (FIG. 1) and is Asn in subtilisin BPN', furin and PC2 but Asp in KEX2. Thus, not all substitutions were clearly predictive of the specificity differences.

A variety of mutants were produced to probe and engineer the specificity of subtilisin BPN' using oligonucleotides described in Table 2.

TABLE 2

Oligonucleotides used for site-directed mutagenesis on subtilisin.

| Mutant | Oligonucleotide | Specificity Pocket | Activity Expressed |
|---|---|---|---|
| S33D | 5'-GCGGTTATCGACG*A*CGGTATCGATTCT -3' (SEQ ID NO: 22) | S2 | + |
| S33K | 5'-GCGGTTATCGACAA*A*G*GTATCGATTCT -3' (SEQ ID NO: 23) | S2 | + |
| S33E | 5'-GCGGTTATCGACG*A*A*GGTATCGATTCT -3' (SEQ ID NO: 24) | S2 | + |
| N62D | 5'-CCAAGACAACG*ACTCTCACGGAA -3' (SEQ ID NO: 25) | S2 | + |
| N62S | 5'-CCAAGACAACAG*CTCTCACGGAA -3' (SEQ ID NO: 26) | S2 | + |
| N62K | 5'-CCAAGACAACAAA*TCTCACGGAA -3' (SEQ ID NO: 27) | S2 | + |
| G166D | 5'-CACTTCCGGCAGCTCG*T*C*G*ACAGTGGA*C*T ACCCTGGC.AAATA-3' (SEQ ID NO: 28) (Inserts Sal I site) | S1 | + |
| G166E | 5'-CACTTCCGGCAGCTCG*T*C*G*ACAGTGGA*GT ACCCTGGCAAATA-3' (SEQ ID NO: 29) (Inserts Sal I site) | S1 | + |
| G128P/P129A | 5'-TTAACATGAGCCTCGGCC*C*AG*CTA*G*C*GGT TCTGCTGCTTTA -3' (SEQ ID NO: 30) (Inserts Nhe I site) | S1 | − |

TABLE 2-continued

Oligonucleotides used for site-directed mutagenesis on subtilisin.

| Mutant | Oligonucleotide | Specificity Pocket | Activity Expressed |
|---|---|---|---|
| G128P/P129A/ S130D/G131D | 5'-TTAACATGAGCCTCGGCC*C*C*G*CGG*A*TGA*TTCTGCTGCTTTAAA -3' (SEQ ID NO: 31) (Inserts Sac II site) | S1 | – |
| T164N/V165D | 5'-CGGCAGCTCAAGCA*A*C*G*A*T*GGCTAT*CCT GGCAAATACCCTTCTGTCA -3' (SEQ ID NO: 32) (Inserts BsaBI site) | S1 | – |
| T164Y/V165D | 5'-CGGCAGCTCAAGCA*A*G*G*A*T*GGCTAT*CCT GGCAAATACCCTTCTGTCA -3' (SEQ ID NO: 32) (Inserts BsaBI site) | S1 | – |
| T164N-Y(insert)-V165D | 5'-ACTTCCGGCAGCTCT*T*C*G*AA*C*T*A*C*G*A *C*GGGTACCCTGGCAAATA-3' (SEQ ID NO: 33) (Inserts BstBI site) | S1 | – |
| N62D/G166D | See individual mutations | S1/S2 | + |
| N62D/G166E | See individual mutations | S1/S2 | + |

*Asterisks indicate base changes from the pSSb (wild-type) template.

After producing the mutant plasmids they were transformed into a protease deficient strain of *B. subtilis* (BG2036) that lacks an endogenous gene for secretion of subtilisin. These were then tested for protease activity on skim milk plates.

The first set of mutants tested were ones where segments of the S1 binding site were replaced with sequences from KEX2. None of these segment replacements produced detectable activity on skim milk plates even though variants of subtilisin whose catalytic efficiencies are reduced by as much as 1000-fold do produce detectable halos (Wells, J. A., Cunningham, B. C., Graycar, T. P. and Estell, D. A. (1986) *Philos. Trans. R. Soc. Lond.* A. 317.415423). We went on to produce single residue substitutions that should have less impact on the stability. These mutants at positions 166 in the S1 site, and 33 and 62 in the S2 site, were chosen based on the modeling and sequence considerations described above. Fortunately all single mutants as well as combination mutants produced activity on skim milk plates and could be purified to homogeneity.

Kinetic Analysis of Variant Subtilisins.

Figure 2:
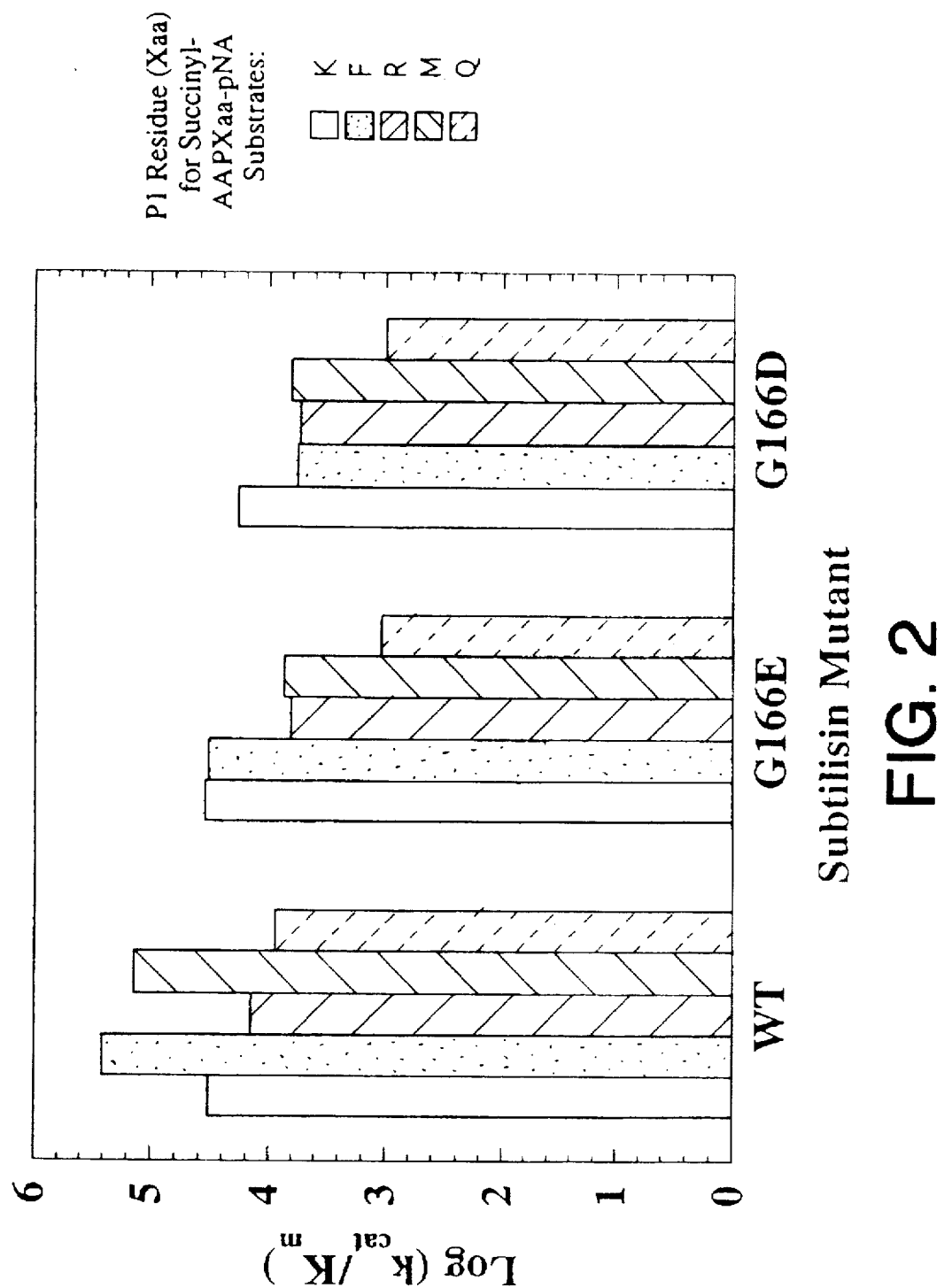
FIG. 2. Kinetic analysis of S1 binding site subtilisin mutants versus substrates having variable P1 residues. The kinetic constant $k_{cat}/K_m$ was determined from plots of initial rates versus substrate concentration for the tetrapeptide series succinyl-Ala-Ala-Pro-Xaa-pNa (SEQ ID NO: 69) , were Xaa was Lys (SEQ ID NO: 58), Arg (SEQ ID NO: 59), Phe (SEQ ID NO: 56), Met (SEQ ID NO: 60) or Gln (SEQ ID NO: 61) (defined to the right of the plot).

To probe the effects of the G166E and G166D on specificity at the P1 position we used substrates having the form suc-AAPX-pna (SEQ ID NO: 69) where X was either Lys (SEQ ID NO: 58), Arg (SEQ ID NO: 59), Phe (SEQ ID NO: 56), Met (SEQ ID NO: 60) or Gln (SEQ ID NO: 61). The $k_{cat}$/Km values were determined from initial rate measurements and results reported in FIG. 2. Whereas the wild-type enzyme preferred Phe>Met>Lys>Arg>Gln, the G166E preferred Lys~Phe>Arg~Met>Gln, and G166D preferred Lys>Phe~Arg~Met>Gln. Thus, both the acidic substitutions at position 166 caused a shift in preference for basic residues as previously reported (Wells, J. A., Powers, D. B., Bott, R. R., Graycar, T. P. and Estell, D. A. (1987a), *Proc. Natl. Acad. Sci. USA* 84:1219–1223).

Figure 3:
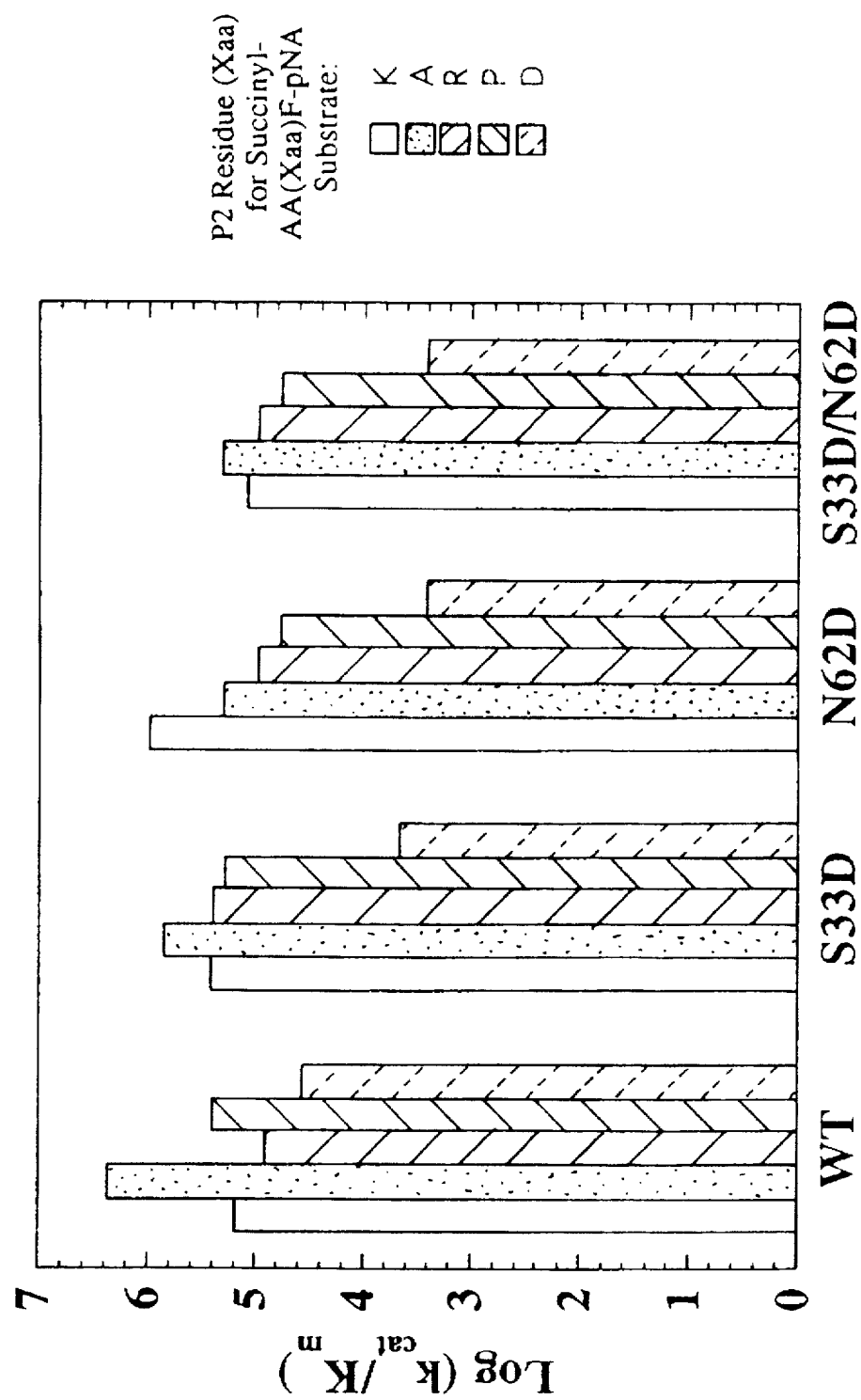
FIG. 3. Kinetic analysis of S2 binding site subtilisin mutants versus substrates having variable P2 residues. The kinetic constant $k_{cat}/K_m$ was determined from plots of initial rates versus substrate concentration for the tetrapeptide series succinyl-Ala-Ala-Xaa-Phe-pNa (SEQ ID NO: 70), were Xaa was Lys (SEQ ID NO: 62), Arg (SEQ ID NO: 64), Ala (SEQ ID NO: 63), Pro (SEQ ID NO: 56), or Asp (SEQ ID NO: 65) (defined on the right of the plot).

The effects of single and double substitutions in the S2 binding site were analyzed with substrates having the form, suc-Ala-Ala-X-Phe-pna and are shown in FIG. 3. At the P2 position the wild-type enzyme preferred Ala>Pro>Lys>Arg>Asp. In contrast, the S33D preferred Ala>Lys~Arg~Pro>Asp and the N62D preferred Lys>Ala>Arg>Pro>Asp. Although the effects were most dramatic for the N62D mutant, the S33D variant also showed significant improvement toward basic P2 residues and corresponding reduction in hydrolysis of the Ala and Asp P2 substrates. We then analyzed the double mutant, but found it exhibited the catalytic efficiency of the worse of the two single mutants for each of the substrates tested.

Figure 4:
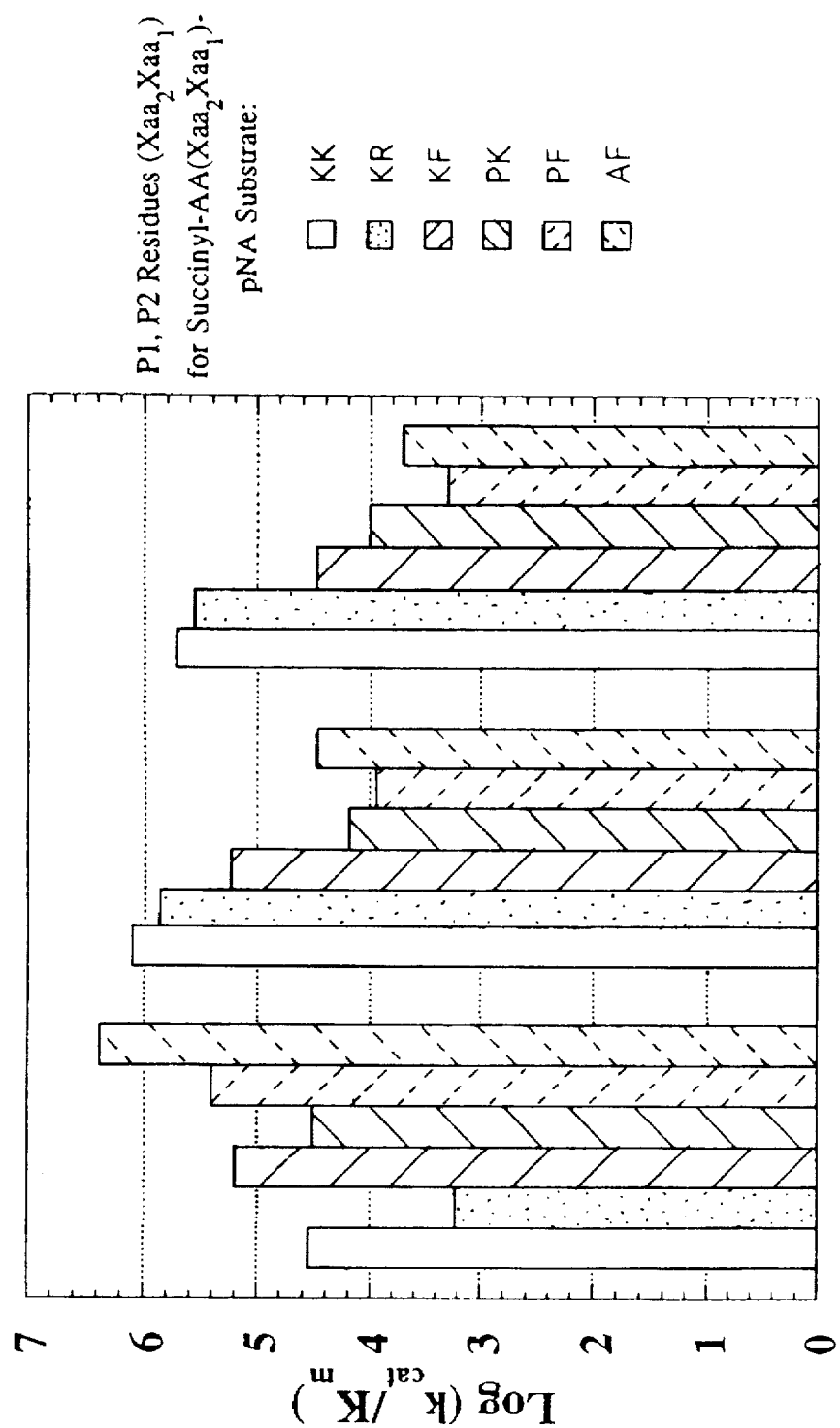
FIG. 4. Kinetic analysis of combined S1 and S2 binding site subtilisin mutants versus substrates having variable P1 and P2 residues. The kinetic constants $k_{cat}/K_m$ were determined from plots of initial rates versus substrate concentration for the tetrapeptide series succinyl-Ala-Ala-Xaa$_2$-Xaa$_1$-pNa (SEQ ID NO: 71), were Xaa$_2$-Xaa$_1$ was Lys-Lys (SEQ ID NO: 66), Lys-Arg (SEQ ID NO: 67), Lys-Phe (SEQ ID NO: 62), Pro-Lys (SEQ ID NO: 58), Pro-Phe (SEQ ID NO: 56), or Ala-Phe (SEQ ID NO: 63) (defined on the right of the plot).

Despite the less than additive effects seen for the two charged substitutions in the S2 site, we decided to combine the best S2 site variant (N62D) with either of the acidic substitutions in the S1 site. The two double mutants, N62D/G166E and N62D/G166D, were analyzed with substrates having the form, suc-AAXX-pna (SEQ ID NO: 71) where XX was either KK (SEQ ID NO: 66), KR (SEQ ID NO: 67), KF (SEQ ID NO: 62), PK (SEQ ID NO: 58), PF (SEQ ID NO: 56) or AF (SEQ ID NO: 63)(FIG. 4). The wild-type preference was AF>PF~KF>KK~PK>KR, whereas the double mutants had the preference KK>KR>KF>PK~AF>PF. Thus for the double mutants there was a dramatic improvement toward cleavage of dibasic substrates and away from cleaving the hydrophobic substrates.

The greater than additive effect (or synergy) of these mutants can be seen from ratios of the catalytic efficiencies for the single and multiple mutants. For example, the G166E variant cannot distinguish Lys from Phe at the P1 position. Yet the N62D/G166E variant cleaves the Lys-Lys substrate about 8 times faster than the Lys-Phe substrate. Similarly the G166D cleaves the Lys P1 substrate about 3 times faster than the Phe P1 substrate, but the N62D/G166D double mutant cleaves a Lys-Lys substrate 18 times faster than a Lys-Phe substrate. Thus, as opposed to the reduction in specificity seen for the double mutant in the S2 site, the S1-S2 double mutants enhance specificity for basic residues. It is possible that these two sites bind the dibasic substrates in a cooperative manner analogous to a chelate effect.

Substrate Phage Selection and Cleavage of a Fusion Protein

Subtilisin has the capability to bind substrates from the P4 to P3' positions (McPhalen, C. A. and James, N. G. (1988) *Biochemistry* 27:6582–6598 and Bode, W., Papamokos, E., Musil, D., Seemueller, U. and Fritz, M. (1986) *EMBO J.* 5:813–818). Given this extensive binding site and the apparent cooperative nature in the way the substrate can bind the enzyme we wished to explore more broadly the substrate preferences for the enzyme. To do this we utilized a method we call substrate phage selection (Matthews, D. J., Goodman, L. J., Gorman, C. M., and Wells, J. A. (1994) *Protein Science* 3:1197–1205 and Matthews, D. J. and Wells, J. A. (1993) *Science* 260:1113–1117). In this method a five-residue substrate linker that was flanked by diglycine residues is inserted between an affinity domain (in this case a high affinity variant of hGH) and the carboxy-termnal domain of gene III, a minor coat protein displayed on the surface of the filamentous phage, M13. The five residue substrate linker is fully randomized to generate a library of $20^5$ different protein sequence variants. These are displayed on the phage particles which are allowed to bind to the hGHbp. The protease of interest is added and if it cleaves the phage particle at the substrate linker it will release that particle. The particles released by protease treatment can be propagated and subjected to another round of selection to further enrich for good protease substrates. Sequences that are retained can also be propagated to enrich for poor protease substrates. By sequencing the isolated phage genes at the end of either selection one can identify good and poor substrates for further analysis.

We chose to focus on the subtilisin BPN' variant N62D/G166D as it was slightly better at discriminating the synthetic dibasic substrates from the others. We subjected the substrate phage library to nine rounds of selection with the subtilisin variant and isolated clones that were either increasingly sensitive or resistant to cleavage. Of twenty-one clones sequenced from the sensitive pool eighteen contained dibasic residues, eleven of which had the substrate linker sequence Asn-Leu-Met-Arg-Lys (SEQ ID NO: 35) (Table 3).

TABLE 3

Substrate phage sequences sensitive or resistant to N62D/G166D subtilisin from a GG-xxxxx-GG library after 9 rounds of selection[a].

| Protease Sensitive Pool | | |
|---|---|---|
| No Basic Sites (0) | Monobasic Sites (3) | Dibasic Sites (18) |
| | N L T A R (3) (SEQ ID NO: 34) | N L M R K (11) (SEQ ID NO: 35) |
| | | T A S R R (4) (SEQ ID NO: 36) |
| | | L T R R S (SEQ ID NO: 37) |
| | | A L S R K (SEQ ID NO: 38) |
| | | L M L R K (SEQ ID NO: 39) |

| Protease Resistant Pool | | |
|---|---|---|
| No Basic Sites (7) | Monobasic Sites (2) | Dibasic Sites (1) |
| A S T H F (SEQ ID NO: 40) | Q K P N F (SEQ ID NO: 41) | R K P T H (SEQ ID NO: 42) |
| I Q Q Q Y (SEQ ID NO: 43) | R P G A M (SEQ ID NO: 44) | |
| Q G E L P (SEQ ID NO: 45) | | |
| A P D P T (SEQ ID NO: 46) | | |
| Q L L E H (SEQ ID NO: 47) | | |
| V N N N H (SEQ ID NO: 48) | | |
| A Q S N L (SEQ ID NO: 49) | | |

[a]Numbers in parentheses indicate the number of times a particular DNA sequence was isolated.

Three (3) of the sensitive sequences were monobasic, Asn-Leu-Thr-Ala-Arg (SEQ ID NO: 34). It is known that subtilisin has a preference for hydrophobic residues at the P4 position. If these and the other selected substrates were indeed cleaved after the last basic residue they all would have a Leu, Met or Ala at the P4 position. Almost no basic residues were isolated in the protease resistant pool and those that were had a Pro following the mono- or dibasic residue. It is known that subtilisin does not cleave substrates containing Pro at the P1' position (Carter, P., Nilsson, B., Burnier, J., Burdick, D. and Wells, J. A. |1989| *Proteins: Struct., Funct., Genet.* 6:240–248). Thus, di-basic substrates where highly selected and these had the additional feature of Leu, Met or Ala at the P4 position.

We wished to analyze how efficiently the most frequently selected sequences were cleaved in the context of a fusion protein. For this we applied an alkaline phosphatase-fusion protein assay (Matthews, D. J., Goodman, L. J., Gorman, C. M., and Wells, J. A. |1994|*Protein Science* 3:1197–1205 and Matthews, D. J. and Wells, J. A. |1993|*Science* 260:1113–1117). The hGH substrate linker domains were excised from the phage vector by PCR and fused in front of the gene for *E. coli* AP. The fusion protein was expressed and purified on an hGH receptor affinity column. The fusion protein was bound to the hGH receptor on a plate and treated with the subtilisin variant. The rate of cleavage of the fusion protein from the plate was monitored by collecting soluble fractions as a function of time and assaying for AP activity (FIG. 5). The most frequently isolated substrate sequence, Asn-Leu-Met-Arg-Lys (SEQ ID NO: 35) was cleaved about ten times faster than the next most frequently isolated clones (Thr-Ala-Ser-Arg-Arg (SEQ ID NO: 50) and Asn-Leu-Thr-Ala-Arg (SEQ ID NO: 34)). We also tested the dibasic sequence isolated from the resistant pool, namely Arg-Lys-Pro-Thr-His (SEQ ID NO: 42). We observed no detectable cleavage above background for this substrate during the assay.

Cleavage of a Fusion Proteins With Subtilisin Variants

A fusion protein is any polypeptide that contains within it an affinity domain (AD) that usually aids in protein purification, a protease cleavage sequence or substrate linker (SL), which is cleaved by a protease and a protein product of interest (PP). Such fusion proteins are generally expressed by recombinant DNA technology. The genes for fusion proteins are designed so that the SL is between the AD and PP. These usually take the form AD-SL-PP such that the domain closest to the N-terminus is AD and PP is closest to the C-terminus.

Examples of AD would include, glutathione-Stransferase which binds to glutathione, protein A (or derivatives or fragments thereof) which binds IgG molecules, poly-histidine sequences, particularly (His)$_6$ (SEQ ID NO: 51) that bind metal affinity columns, maltose binding protein that binds maltose, human growth hormone that binds the human growth hormone receptor or any of a variety of other proteins or protein domains that can bind to an immobilized affinity support with an association constant (Ka) of $>10^5$ $M^{-1}$.

The SL can be any sequence which is cleaved by the N62D/G166D subtilisin variant but preferably ones with di-basic residues. The SL should be at least four residues and preferably contain a large hydrophobic residue at P4 (such as Leu or Met) and dibasic residues at P2 and P1 (such as Arg and Lys). A particularly good substrate is Leu-Met-Arg-Lys- (SEQ ID NO: 52), but a variety of other sequences may work including Ala-Ser-Arg-Arg (SEQ ID NO: 50) and even Leu-Thr-Ala-Arg (SEQ ID NO: 53). It is often useful that the SL contain a flexible segment on its N-terminus to better separate it from the AD and PP. Such sequences include Gly-Pro-Gly-Gly (SEQ ID NO: 54) but can be as simple as Gly-Gly or Pro-Gly. Thus, an example of a particularly good SL would have the sequence Gly-Pro-Gly-Gly-Leu-Met-Arg-Lys (SEQ ID NO: 55). This sequence would be inserted between the AD and PP domains.

The PP can be virtually any protein or peptide of interest but preferably should not have a Pro, Ile, Thr, Val, Asp or Glu as its first residue (P1'), or Pro or Gly at the second residue (P2') or Pro at the third residue (P3'). Such residues are poor substrates for the enzyme and may impair the ability of the N62D/G166D subtilisin variant to cleave the SL sequence.

The conditions for cleaving the fusion protein are best done in aqueous solution, although it should be possible to immobilize the enzyme and cleave the soluble fusion protein. It may also be possible to cleave the fusion protein as it remains immobilized on a solid support (e.g. bound to the solid support through AD) with the soluble N62D/G166D subtilisin variant. It is preferable to add the enzyme to the fusion protein so that the enzyme is less than one part in 100 (1:100) by weight. A good buffer is 10–50 mM Tris (pH 8.2) in 10 mM NaCl. A preferable temperature is about 25° C. although the enzyme is active up to 65° C. The extent of cleavage can be assayed by applying samples to SDS-PAGE. Generally suitable conditions for using the subtilisin variants of this invention do not depart substantially from those known in the art for the use of other subtilisins.

EXAMPLES

In the examples below and elsewhere, the following abbreviations are employed: subtilisin BPN', subtilisin from *Bacillus amyloliquefaciens*; Boc-RVRR-MCA (SEQ ID NO: 73), N-t-butoxy carbonyl-arginine-valine-arginine-arginine-7-amido4-methyl coumarin (SEQ ID NO: 73); suc-Ala-Ala-Pro-Phe-pna (SEQ ID NO: 56), N-succinyl-alanine-alanine-proline-phenylalanyl-p-nitroanalide (SEQ ID NO: 56); hGH, human growth hormone; hGHbp, extracellular domain of the hGH receptor; PBS, phosphate buffered saline; AP, alkaline phosphatase;

Example 1

Construction and Purification of Subtilisin Mutants.

Site-directed mutations were introduced into the subtilisin BPN' gene cloned into the phagemid pSS5 (Wells, J. A., Ferrari, E., Henner, D. J., Estell, D. A. and Chen, E. Y. [1983] *Nucl. Acids Res.* 11:7911–7929). Single-stranded uracil-containing pSS5 template was prepared and mutagenesis performed using the method of Kunkel (Kunkel, T. A., Bebenek, K and McClary, J. [1991] *Methods Enzymol.* 204:125–139). For example, the synthetic oligonucleotide N62D, (5'-CCAAGACAACG*ACTCTCACGGAA-3') (SEQ ID NO: 25)

in which the asterisk denotes a mismatch to the wild-type sequence, was used to construct the N62D mutant. The oligonucleotide was first phosphorylated at the 5' end using T4 polynucleotide kinase according to a described procedure (Sambrook, J., Fritsch, E. F., and Maniatis, T. (1989) in "Molecular Cloning: A Laboratory Manual," Second Edition, Cold Spring Harbor, N.Y.). The phosphorylated oligonucleotide was annealed to single-stranded uracil-containing pSS5 template, the complementary DNA strand was filled in with deoxynucleotides using T7 polynucleotide kinase, and the resulting nicks ligated using T4 DNA ligase according to a previously described procedure (Sambrook, J., Fritsch, E. F., and Maniatis, T. (1989) in "Molecular Cloning: A Laboratory Manual," Second Edition, Cold Spring Harbor, N.Y.). Heteroduplex DNA was transformed into the *E. coli* host JM101(Yanish-Perron, C., Viera, J., and Messing, J. (1985) Gene 33: 103–199), and putative mutants were confirmed by preparation and dideoxy nucleotide sequencing of single stranded DNA (Sanger, F., Nicklen, S. and Coulson, A. R. (1977) *Proc. Natl. Acad. Sci. USA* 74:5463–5467) according to the Sequenase® protocol (USB Biochemicals). Mutant single-stranded DNA was then retransformed into JM101 cells and double stranded DNA prepared according to a previously described procedure (Sambrook, J., Fritsch, E. F., and Maniatis, T. (1989) in "Molecular Cloning: A Laboratory Manual," Second Edition, Cold Spring Harbor, N.Y.). For other mutations also requiring the use of one primer, the oligonucleotides used are listed in Table 2. For several of these oligonucleotides, additional silent mutations emplacing new restriction sites were simultaneously introduced to provide an alternative verification of mutagenesis.

To construct the double mutants N62D/G166D, and N62D/G166E, pSS5 DNA containing the N62D mutation was produced in single-stranded uracil-containing form using the Kunkel procedure (Kunkel, T. A., Bebenek, K and McClary, J. (1991) *Methods Enzymol.* 204, 125–139). This mutant DNA was used as template for the further introduction of the G166D or G166E mutations, using the appropriate oligonucleotide primers (see sequences in Table 2), following the procedures described above.

For expression of the subtilisin BPN' mutants, double stranded mutant DNA was transformed into a protease-deficient strain (BG2036) of *Bacillus Subtilis* (Yang, M. Y., Ferrari, E. and Henner, D. J. (1984) *Journal of Bacteriology* 160:15–21) according to a previous method (Anagnostopolouus, C. and Spizizen, J. (1961) *Journal of Bacteriology* 81:741–746) in which transformation mixtures were plated out on LB plus skim milk plates containing 12.5 µg/mL chloramphenicol. The clear halos indicative of skim milk digestion surrounding transformed colonies were noted to roughly estimate secreted protease activity.

The transformed BG2036 strains were cultured by inoculating 5 mL of 2×YT media (Miller, J. H., (1972) in "Experiments in Molecular Genetics," Cold Spring Harbor, N.Y.) containing 12.5 µg/mL chloramphenicol and 2 mM $CaCl_2$ at 37° C. for 18–20 h, followed by 1:100 dilution in the same medium and growth in shake flasks at 37° C. for 18–22 h with vigorous aeration. The cells were harvested by centrifugation (6000 g, 15 min, 4° C.), and to the supernatant 20 mM (final) $CaCl_2$ and one volume of ethanol (−20° C.) were added. After 30 min at 4° C., the solution was centrifuged (12,000 g, 15 min, 4° C.), and one volume of ethanol (−20° C.) added to the supernatant. After 2 h at −20° C., the solution was centrifuged (12,000 g, 15 min., 4° C.) and the pellet resuspended in and dialyzed against MC (25 mM 2-[N-Morpholino]ethanesulfonic acid (MES), 5 mM $CaCl_2$ at pH 5.5) overnight at 4° C. The dialysate was passed through a 0.22 µm syringe filter and loaded onto a mono-S cation exchange column run by an FPLC system (Pharmacia Biotechnology). The column was washed with 20 volumes of MC and mutant subtilisin eluted over a linear gradient of zero to 0.15M NaCl in MC, all at a flow rate of 1 mL/min. Peak fractions were recovered and the subtilisin mutant quantitated by measuring the absorbance at 280 nm ($E_{280}$ 0.1% =1.17) (Matsubara, H.; Kasper, C. B.; Brown, D. M.; and Smith, E. L. (1965) *J. Biol. Chem.*, 240:1125–1130.).

Example 2

Kinetic Characterizations

Subtilisins were assayed by measuring the initial rates of hydrolysis of p-nitroanilide tetrapeptide substrates in 0.4 mL

17

20 mM Tris-Cl pH 8.2, 4% (v/v) dimethyl sulfoxide at (25±0.2)° C. as described previously (Estell, D. A., Graycar, T. P., Miller, J. V., Powers, D. B., Burnier, J. P., Ng, P. G. and Wells, J. A. |1986| *Science 233:659–663*). Enzyme concentrations $|E|_0$ were determined spectrophotometrically using $E_{280\ nm}0.1\%=1.17$ (Matsubara, H.; Kasper, C. B.; Brown, D. M.; and Smith, E. L. (1965) *J. Biol. Chem.*, 240:1125–1130.), and were typically 5–50 nM in reactions. Initial rates were determined for nine to twelve different substrate concentrations over the range of 0.001–2.0 mM. Plots of initial rates (v) versus substrate concentration |S| were fitted to the Michaelis-Menton equation.

$$v=\frac{k_{cat}|E|_0(|S|)}{K_m+|S|}$$

to determine the kinetic constants $k_{cat}$ and $K_m$ (Fersht, A. in "Enzyme Structure and Mechanism", Second edition, Freeman and Co., N.Y.) using the program Kaleidagraph (Synergy Software, Reading, Pa.).

Example 3

Substrate Phage

Substrate phage selections were performed as described by Matthews and Wells (Matthews, D. J. and Wells, J. A. (1993) *Science* 260:1113–1117), with minor modifications. Phage sorting was carried out using a library in which the linker sequence between the gene III coat protein and a tight-binding variant of hGH was GPGGX₅GGPG (SEQ ID NO: 57). The library contained 2×10⁶ independent transformants. Phage particles were prepared by infecting 1 mL of log phase 27C7 (F⁻/tet^R/Ompt⁻/degP⁻) *Escherichia coli* with ~10⁸ library phage for 1 h at 37° C., followed by 18–24 h of growth in 25 mL 2YT medium containing 10¹⁰ M13K07 helper phage and 50 μg/mL carbenicillin at 37° C. Wells of a 96-well Nunc Maxisorb microtiter plate were coated with 2 μg/mL of hGHbp in 50 mM NaHCO₃ at pH 9.6 overnight at 4° C. and blocked with PBS (10 mM sodium phosphate at pH 7.4 nd 150 mM NaCl) containing 2.5% (w/v) skim milk for 1 h at room temperature. Between 10¹¹ and 10¹² phage in 0.1 mL 10 mM tris-Cl (pH 7.6), 1 mM EDTA, and 100 mM NaCl were incubated in the wells at room temperature for 2 h with gentle agitation. The plate was washed first with 20 rinses of PBS plus 0.05% Tween 20 and then twice with 20 mM tris-Cl at pH 8.2. The N62D/G166D subtilisin was added in 0.1 mL of 20 mM tris-Cl at pH 8.2 and protease sensitive phage were eluted after a variable reaction time. The concentration of protease and incubation times for elution of sensitive phage were decreased gradually over the course of sorting procedure to increase selectivity, with protease concentrations of 0.2 nM (rounds 1–3) and 0.1 nM (rounds 4–9), and reaction times of 5 min (rounds 1–6), 2.5 min (round 7), 40 s (round 8) and 20 s (round 9). Control wells in which no protease was added were also included in each round. For the resistant phage pool, the incubation time with protease remained constant at 5 min. The wells were then washed ten times with PBS plus 0.05% Tween 20 and resistant phage eluted by treatment with 0.1 mL of 0.2M glycine at pH 2.0 in PBS plus 0.05% Tween 20 for 1 min at room temperature. Protease sensitive and resistant phage pools were titered and used to infect log phase 27C7 cells for 1 h at 37° C., followed by centrifugation at 4000 rpm, removal of supernatant, and resuspension in 1 mL 2YT medium. The infected cells were then grown 18–24 h in the presence of helper phage as described above and the process repeated 9 times. Selected substrates were introduced into AP fusion proteins and assayed for relative rates of cleavage as described by Matthews and Wells (Matthews, D. J., Goodman, L. J., Gorman, C. M., and Wells, J. A. (1994) *Protein Science* 3:1197–1205 and Matthews, D. J. and Wells, J. A. (1993)Science 260:1113–1117), except that the cleavage reactions were performed in 20 mM Tris-Cl at pH 8.2.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the ends of the present invention.

All references cited herein are expressly incorporated by reference.

SEQUENCE LISTING ( 1 ) GENERAL INFORMATION:

( i i i ) NUMBER OF SEQUENCES: 74

( 2 ) INFORMATION FOR SEQ ID NO:1:

( i ) SEQUENCE CHARACTERISTICS:
( A ) LENGTH: 8119 base pairs
( B ) TYPE: Nucleic Acid
( C ) STRANDEDNESS: Single
( D ) TOPOLOGY: Linear ( x i ) SEQUENCE DESCRIPTION: SEQ ID NO:1:

```
GAATTCNGGT  CTACTAAAAT  ATTATTCCAT  ACTATACAAT  TAATACACAG              50

AATAATCTGT  CTATTGGTTA  TTCTGCAAAT  GAAAAAAAGG  AGAGGATAAA             100

GA   GTG  AGA  GGC  AAA  AAA  GTA  TGG  ATC  AGT  TTG  CTG  TTT        138
     Val  Arg  Gly  Lys  Lys  Val  Trp  Ile  Ser  Leu  Leu  Phe
     -107 -105            -100

GCT  TTA  GCG  TTA  ATC  TTT  ACG  ATG  GCG  TTC  GGC  AGC  ACA        177
```

| Ala | Leu | Ala | Leu | Ile | Phe | Thr | Met | Ala | Phe | Gly | Ser | Thr | |
|-----|-----|-----|-----|-----|-----|-----|-----|-----|-----|-----|-----|-----|---|
| -95 | | | | -90 | | | | | -85 | | | | |

| TCC | TCT | GCC | CAG | GCG | GCA | GGG | AAA | TCA | AAC | GGG | GAA | AAG | 216 |
|-----|-----|-----|-----|-----|-----|-----|-----|-----|-----|-----|-----|-----|-----|
| Ser | Ser | Ala | Gln | Ala | Ala | Gly | Lys | Ser | Asn | Gly | Glu | Lys | |
| | | -80 | | | | | -75 | | | | | -70 | |

| AAA | TAT | ATT | GTC | GGG | TTT | AAA | CAG | ACA | ATG | AGC | ACG | ATG | 255 |
|-----|-----|-----|-----|-----|-----|-----|-----|-----|-----|-----|-----|-----|-----|
| Lys | Tyr | Ile | Val | Gly | Phe | Lys | Gln | Thr | Met | Ser | Thr | Met | |
| | | | | -65 | | | | | -60 | | | | |

| AGC | GCC | GCT | AAG | AAG | AAA | GAT | GTC | ATT | TCT | GAA | AAA | GGC | 294 |
|-----|-----|-----|-----|-----|-----|-----|-----|-----|-----|-----|-----|-----|-----|
| Ser | Ala | Ala | Lys | Lys | Lys | Asp | Val | Ile | Ser | Glu | Lys | Gly | |
| | -55 | | | | | -50 | | | | | -45 | | |

| GGG | AAA | GTG | CAA | AAG | CAA | TTC | AAA | TAT | GTA | GAC | GCA | GCT | 333 |
|-----|-----|-----|-----|-----|-----|-----|-----|-----|-----|-----|-----|-----|-----|
| Gly | Lys | Val | Gln | Lys | Gln | Phe | Lys | Tyr | Val | Asp | Ala | Ala | |
| | | | -40 | | | | | -35 | | | | | |

| TCA | GCT | ACA | TTA | AAC | GAA | AAA | GCT | GTA | AAA | GAA | TTG | AAA | 372 |
|-----|-----|-----|-----|-----|-----|-----|-----|-----|-----|-----|-----|-----|-----|
| Ser | Ala | Thr | Leu | Asn | Glu | Lys | Ala | Val | Lys | Glu | Leu | Lys | |
| -30 | | | | | -25 | | | | | -20 | | | |

| AAA | GAC | CCG | AGC | GTC | GCT | TAC | GTT | GAA | GAA | GAT | CAC | GTA | 411 |
|-----|-----|-----|-----|-----|-----|-----|-----|-----|-----|-----|-----|-----|-----|
| Lys | Asp | Pro | Ser | Val | Ala | Tyr | Val | Glu | Glu | Asp | His | Val | |
| | | -15 | | | | | -10 | | | | | -5 | |

| GCA | CAT | GCG | TAC | GCG | CAG | TCC | GTG | CCT | TAC | GGC | GTA | TCA | 450 |
|-----|-----|-----|-----|-----|-----|-----|-----|-----|-----|-----|-----|-----|-----|
| Ala | His | Ala | Tyr | Ala | Gln | Ser | Val | Pro | Tyr | Gly | Val | Ser | |
| | | | | 1 | | | | 5 | | | | | |

| CAA | ATT | AAA | GCC | CCT | GCT | CTG | CAC | TCT | CAA | GGC | TAC | ACT | 489 |
|-----|-----|-----|-----|-----|-----|-----|-----|-----|-----|-----|-----|-----|-----|
| Gln | Ile | Lys | Ala | Pro | Ala | Leu | His | Ser | Gln | Gly | Tyr | Thr | |
| 10 | | | | | 15 | | | | | 20 | | | |

| GGA | TCA | AAT | GTT | AAA | GTA | GCG | GTT | ATC | GAC | AGC | GGT | ATC | 528 |
|-----|-----|-----|-----|-----|-----|-----|-----|-----|-----|-----|-----|-----|-----|
| Gly | Ser | Asn | Val | Lys | Val | Ala | Val | Ile | Asp | Ser | Gly | Ile | |
| | | 25 | | | | | 30 | | | | | 35 | |

| GAT | TCT | TCT | CAT | CCT | GAT | TTA | AAG | GTA | GCA | GGC | GGA | GCC | 567 |
|-----|-----|-----|-----|-----|-----|-----|-----|-----|-----|-----|-----|-----|-----|
| Asp | Ser | Ser | His | Pro | Asp | Leu | Lys | Val | Ala | Gly | Gly | Ala | |
| | | | | 40 | | | | | 45 | | | | |

| AGC | ATG | GTT | CCT | TCT | GAA | ACA | AAT | CCT | TTC | CAA | GAC | AAC | 606 |
|-----|-----|-----|-----|-----|-----|-----|-----|-----|-----|-----|-----|-----|-----|
| Ser | Met | Val | Pro | Ser | Glu | Thr | Asn | Pro | Phe | Gln | Asp | Asn | |
| | 50 | | | | | 55 | | | | | 60 | | |

| GAC | TCT | CAC | GGA | ACT | CAC | GTT | GCC | GGC | ACA | GTT | GCG | GCT | 645 |
|-----|-----|-----|-----|-----|-----|-----|-----|-----|-----|-----|-----|-----|-----|
| Asp | Ser | His | Gly | Thr | His | Val | Ala | Gly | Thr | Val | Ala | Ala | |
| | | | 65 | | | | | 70 | | | | | |

| CTT | AAT | AAC | TCA | ATC | GGT | GTA | TTA | GGC | GTT | GCG | CCA | AGC | 684 |
|-----|-----|-----|-----|-----|-----|-----|-----|-----|-----|-----|-----|-----|-----|
| Leu | Asn | Asn | Ser | Ile | Gly | Val | Leu | Gly | Val | Ala | Pro | Ser | |
| 75 | | | | | 80 | | | | | 85 | | | |

| GCA | TCA | CTT | TAC | GCT | GTA | AAA | GTT | CTC | GGT | GCT | GAC | GGT | 723 |
|-----|-----|-----|-----|-----|-----|-----|-----|-----|-----|-----|-----|-----|-----|
| Ala | Ser | Leu | Tyr | Ala | Val | Lys | Val | Leu | Gly | Ala | Asp | Gly | |
| | | 90 | | | | | 95 | | | | | 100 | |

| TCC | GGC | CAA | TAC | AGC | TGG | ATC | ATT | AAC | GGA | ATC | GAG | TGG | 762 |
|-----|-----|-----|-----|-----|-----|-----|-----|-----|-----|-----|-----|-----|-----|
| Ser | Gly | Gln | Tyr | Ser | Trp | Ile | Ile | Asn | Gly | Ile | Glu | Trp | |
| | | | | 105 | | | | | 110 | | | | |

| GCG | ATC | GCA | AAC | AAT | ATG | GAC | GTT | ATT | AAC | ATG | AGC | CTC | 801 |
|-----|-----|-----|-----|-----|-----|-----|-----|-----|-----|-----|-----|-----|-----|
| Ala | Ile | Ala | Asn | Asn | Met | Asp | Val | Ile | Asn | Met | Ser | Leu | |
| 115 | | | | | 120 | | | | | 125 | | | |

| GGC | GGA | CCT | TCT | GGT | TCT | GCT | GCT | TTA | AAA | GCG | GCA | GTT | 840 |
|-----|-----|-----|-----|-----|-----|-----|-----|-----|-----|-----|-----|-----|-----|
| Gly | Gly | Pro | Ser | Gly | Ser | Ala | Ala | Leu | Lys | Ala | Ala | Val | |
| | | | 130 | | | | | 135 | | | | | |

| GAT | AAA | GCC | GTT | GCA | TCC | GGC | GTC | GTA | GTC | GTT | GCG | GCA | 879 |
|-----|-----|-----|-----|-----|-----|-----|-----|-----|-----|-----|-----|-----|-----|
| Asp | Lys | Ala | Val | Ala | Ser | Gly | Val | Val | Val | Val | Ala | Ala | |
| 140 | | | | | 145 | | | | | 150 | | | |

| GCC | GGT | AAC | GAA | GGC | ACT | TCC | GGC | AGC | TCG | TCG | ACA | GTG | 918 |
|-----|-----|-----|-----|-----|-----|-----|-----|-----|-----|-----|-----|-----|-----|
| Ala | Gly | Asn | Glu | Gly | Thr | Ser | Gly | Ser | Ser | Ser | Thr | Val | |
| | | 155 | | | | | 160 | | | | | 165 | |

| GAC | TAC | CCT | GGC | AAA | TAC | CCT | TCT | GTC | ATT | GCA | GTA | GGC | 957 |
|-----|-----|-----|-----|-----|-----|-----|-----|-----|-----|-----|-----|-----|-----|

-continued

| | | | | | | | | | | | | |
|---|---|---|---|---|---|---|---|---|---|---|---|---|
| Asp | Tyr | Pro | Gly | Lys | Tyr | Pro | Ser | Val | Ile | Ala | Val | Gly |
| | | | | 170 | | | | 175 | | | | |

| GCT | GTT | GAC | AGC | AGC | AAC | CAA | AGA | GCA | TCT | TTC | TCA | AGC | 996 |
|---|---|---|---|---|---|---|---|---|---|---|---|---|---|
| Ala | Val | Asp | Ser | Ser | Asn | Gln | Arg | Ala | Ser | Phe | Ser | Ser | |
| | 180 | | | | | 185 | | | | | 190 | | |

| GTA | GGA | CCT | GAG | CTT | GAT | GTC | ATG | GCA | CCT | GGC | GTA | TCT | 1035 |
|---|---|---|---|---|---|---|---|---|---|---|---|---|---|
| Val | Gly | Pro | Glu | Leu | Asp | Val | Met | Ala | Pro | Gly | Val | Ser | |
| | | | 195 | | | | | 200 | | | | | |

| ATC | CAA | AGC | ACG | CTT | CCT | GGA | AAC | AAA | TAC | GGG | GCG | TAC | 1074 |
|---|---|---|---|---|---|---|---|---|---|---|---|---|---|
| Ile | Gln | Ser | Thr | Leu | Pro | Gly | Asn | Lys | Tyr | Gly | Ala | Tyr | |
| 205 | | | | | 210 | | | | | 215 | | | |

| AAC | GGT | ACC | TCA | ATG | GCA | TCT | CCG | CAC | GTT | GCC | GGA | GCG | 1113 |
|---|---|---|---|---|---|---|---|---|---|---|---|---|---|
| Asn | Gly | Thr | Ser | Met | Ala | Ser | Pro | His | Val | Ala | Gly | Ala | |
| | | 220 | | | | 225 | | | | | 230 | | |

| GCT | GCT | TTG | ATT | CTT | TCT | AAG | CAC | CCG | AAC | TGG | ACA | AAC | 1152 |
|---|---|---|---|---|---|---|---|---|---|---|---|---|---|
| Ala | Ala | Leu | Ile | Leu | Ser | Lys | His | Pro | Asn | Trp | Thr | Asn | |
| | | | | 235 | | | | | 240 | | | | |

| ACT | CAA | GTC | CGC | AGC | AGT | TTA | GAA | AAC | ACC | ACT | ACA | AAA | 1191 |
|---|---|---|---|---|---|---|---|---|---|---|---|---|---|
| Thr | Gln | Val | Arg | Ser | Ser | Leu | Glu | Asn | Thr | Thr | Thr | Lys | |
| | 245 | | | | | 250 | | | | | 255 | | |

| CTT | GGT | GAT | TCT | TTC | TAC | TAT | GGA | AAA | GGG | CTG | ATC | AAC | 1230 |
|---|---|---|---|---|---|---|---|---|---|---|---|---|---|
| Leu | Gly | Asp | Ser | Phe | Tyr | Tyr | Gly | Lys | Gly | Leu | Ile | Asn | |
| | | | 260 | | | | | 265 | | | | | |

| GTA | CAG | GCG | GCA | GCT | CAG | TA AAACATAAAA AACCGGCCTT | 1270 |
|---|---|---|---|---|---|---|---|
| Val | Gln | Ala | Ala | Ala | Gln | | |
| 270 | | | | | 275 | | |

| | | | | |
|---|---|---|---|---|
| GGCCCCGCCG | GTTTTTTATT | ATTTTTCTTC | CTCCGCATGT | TCAATCCGCT | 1320 |
| CCATAATCGA | CGGATGGCTC | CCTCTGAAAA | TTTTAACGAG | AAACGGCGGG | 1370 |
| TTGACCCGGC | TCAGTCCCGT | AACGGCCAAG | TCCTGAAACG | TCTCAATCGC | 1420 |
| CGCTTCCCGG | TTTCCGGTCA | GCTCAATGCC | GTAACGGTCG | GCGGCGTTTT | 1470 |
| CCTGATACCG | GGAGACGGCA | TTCGTAATCG | GATCCGGAAA | TTGTAAACGT | 1520 |
| TAATATTTTG | TTAAAATTCG | CGTTAAATTT | TTGTTAAATC | AGCTCATTTT | 1570 |
| TTAACCAATA | GGCCGAAATC | GGCAAAATCC | CTTATAAATC | AAAAGAATAG | 1620 |
| ACCGAGATAG | GGTTGAGTGT | TGTTCCAGTT | TGGAACAAGA | GTCCACTATT | 1670 |
| AAAGAACGTG | GACTCCAACG | TCAAAGGGCG | AAAAACCGTC | TATCAGGGCT | 1720 |
| ATGGCCCACT | ACGTGAACCA | TCACCCTAAT | CAAGTTTTTT | GGGGTCGAGG | 1770 |
| TGCCGTAAAG | CACTAAATCG | GAACCCTAAA | GGGAGCCCCC | GATTTAGAGC | 1820 |
| TTGACGGGGA | AAGCCGGCGA | ACGTGGCGAG | AAAGGAAGGG | AAGAAAGCGA | 1870 |
| AAGGAGCGGG | CGCTAGGGCG | CTGGCAAGTG | TAGCGGTCAC | GCTGCGCGTA | 1920 |
| ACCACCACAC | CCGCCGCGCT | TAATGCGCCG | CTACAGGGCG | CGTCCGGATC | 1970 |
| NGATCCGACG | CGAGGCTGGA | TGGCCTTCCC | CATTATGATT | CTTCTCGCTT | 2020 |
| CCGGCGGCAT | CGGGATGCCC | GCGTTGCAGG | CCATGCTGTC | CAGGCAGGTA | 2070 |
| GATGACGACC | ATCAGGGACA | GCTTCAAGGA | TCGCTCGCGG | CTCTTACCAG | 2120 |
| CCTAACTTCG | ATCACTGGAC | CGCTGATCGT | CACGGCGATT | TATGCCGCCT | 2170 |
| CGGCGAGCAC | ATGGAACGGG | TTGGCATGGA | TTGTAGGCGC | CGCCCTATAC | 2220 |
| CTTGTCTGCC | TCCCGCGTT | GCGTCGCGGT | GCATGGAGCC | GGGCCACCTC | 2270 |
| GACCTGAATG | GAAGCCGGCG | GCACCTCGCT | AACGGATTCA | CCACTCCAAG | 2320 |
| AATTGGAGCC | AATCAATTCT | TGCGGAGAAC | TGTGAATGCG | CAAACCAACC | 2370 |
| CTTGGCAGAA | CATATCCATC | GCGTCCGCCA | TCTCCAGCAG | CCGCACGCGG | 2420 |

-continued

| | | | | |
|---|---|---|---|---|
| CGCATCTCGG | GCCGCGTTGC | TGGCGTTTTT | CCATAGGCTC | CGCCCCCCTG | 2470
| ACGAGCATCA | CAAAAATCGA | CGCTCAAGTC | AGAGGTGGCG | AAACCCGACA | 2520
| GGACTATAAA | GATACCAGGC | GTTTCCCCCT | GGAAGCTCCC | TCGTGCGCTC | 2570
| TCCTGTTCCG | ACCCTGCCGC | TTACCGGATA | CCTGTCCGCC | TTTCTCCCTT | 2620
| CGGGAAGCGT | GGCGCTTTCT | CAATGCTCAC | GCTGTAGGTA | TCTCAGTTCG | 2670
| GTGTAGGTCG | TTCGCTCCAA | GCTGGGCTGT | GTGCACGAAC | CCCCGTTCA | 2720
| GCCCGACCGC | TGCGCCTTAT | CCGGTAACTA | TCGTCTTGAG | TCCAACCCGG | 2770
| TAAGACACGA | CTTATCGCCA | CTGGCAGCAG | CCACTGGTAA | CAGGATTAGC | 2820
| AGAGCGAGGT | ATGTAGGCGG | TGCTACAGAG | TTCTTGAAGT | GGTGGCCTAA | 2870
| CTACGGCTAC | ACTAGAAGGA | CAGTATTTGG | TATCTGCGCT | CTGCTGAAGC | 2920
| CAGTTACCTT | CGGAAAAAGA | GTTGGTAGCT | CTTGATCCGG | CAAACAAACC | 2970
| ACCGCTGGTA | GCGGTGGTTT | TTTTGTTTGC | AAGCAGCAGA | TTACGCGCAG | 3020
| AAAAAAAGGA | TCTCAAGAAG | ATCCTTTGAT | CTTTTCTACG | GGGTCTGACG | 3070
| CTCAGTGGAA | CGAAAACTCA | CGTTAAGGGA | TTTTGGTCAT | GAGATTATCA | 3120
| AAAAGGATCT | TCACCTAGAT | CCTTTTAAAT | TAAAAATGAA | GTTTTAAATC | 3170
| AATCTAAAGT | ATATATGAGT | AAACTTGGTC | TGACAGTTAC | CAATGCTTAA | 3220
| TCAGTGAGGC | ACCTATCTCA | GCGATCTGTC | TATTTCGTTC | ATCCATAGTT | 3270
| GCCTGACTCC | CCGTCGTGTA | GATAACTACG | ATACGGGAGG | GCTTACCATC | 3320
| TGGCCCCAGT | GCTGCAATGA | TACCGCGAGA | CCCACGCTCA | CCGGCTCCAG | 3370
| ATTTATCAGC | AATAAACCAG | CCAGCCGGAA | GGGCCGAGCG | CAGAAGTGGT | 3420
| CCTGCAACTT | TATCCGCCTC | CATCCAGTCT | ATTAATTGTT | GCCGGGAAGC | 3470
| TAGAGTAAGT | AGTTCGCCAG | TTAATAGTTT | GCGCAACGTT | GTTGCCATTG | 3520
| CTGCAGGCAT | CGTGGTGTCA | CGCTCGTCGT | TTGGTATGGC | TTCATTCAGC | 3570
| TCCGGTTCCC | AACGATCAAG | GCGAGTTACA | TGATCCCCCA | TGTTGTGCAA | 3620
| AAAAGCGGTT | AGCTCCTTCG | GTCCTCCGAT | CGTTGTCAGA | AGTAAGTTGG | 3670
| CCGCAGTGTT | ATCACTCATG | GTTATGGCAG | CACTGCATAA | TTCTCTTACT | 3720
| GTCATGCCAT | CCGTAAGATG | CTTTTCTGTG | ACTGGTGAGT | ACTCAACCAA | 3770
| GTCATTCTGA | GAATAGTGTA | TGCGGCGACC | GAGTTGCTCT | TGCCCGGCGT | 3820
| CAACACGGGA | TAATACCGCG | CCACATAGCA | GAACTTTAAA | AGTGCTCATC | 3870
| ATTGGAAAAC | GTTCTTCGGG | GCGAAAACTC | TCAAGGATCT | TACCGCTGTT | 3920
| GAGATCCAGT | TCGATGTAAC | CCACTCGTGC | ACCCAACTGA | TCTTCAGCAT | 3970
| CTTTTACTTT | CACCAGCGTT | TCTGGGTGAG | CAAAAACAGG | AAGGCAAAAT | 4020
| GCCGCAAAAA | AGGGAATAAG | GGCGACACGG | AAATGTTGAA | TACTCATACT | 4070
| CTTCCTTTTT | CAATATTATT | GAAGCATTTA | TCAGGGTTAT | TGTCTCATGA | 4120
| GCGGATACAT | ATTTGAATGT | ATTTAGAAAA | ATAAACAAAT | AGGGGTTCCG | 4170
| CGCACATTTC | CCCGAAAAGT | GCCACCTGAC | GTCTAAGAAA | CCATTATTAT | 4220
| CATGACATTA | ACCTATAAAA | ATAGGCGTAT | CACGAGGCCC | TTTCGTCTTC | 4270
| AAGAATTAAT | TCCTTAAGGA | ACGTACAGAC | GGCTTAAAAG | CCTTTAAAAA | 4320
| CGTTTTTAAG | GGGTTTGTAG | ACAAGGTAAA | GGATAAAACA | GCACAATTCC | 4370
| AAGAAAAACA | CGATTTAGAA | CCTAAAAAGA | ACGAATTTGA | ACTAACTCAT | 4420

```
AACCGAGAGG  TAAAAAAAGA  ACGAAGTCGA  GATCAGGGAA  TGAGTTTATA      4470
AAATAAAAAA  AGCACCTGAA  AAGGTGTCTT  TTTTTGATGG  TTTTGAACTT      4520
GTTCTTTCTT  ATCTTGATAC  ATATAGAAAT  AACGTCATTT  TTATTTTAGT      4570
TGCTGAAAGG  TGCGTTGAAG  TGTTGGTATG  TATGTGTTTT  AAAGTATTGA      4620
AAACCCTTAA  AATTGGTTGC  ACAGAAAAAC  CCCATCTGTT  AAAGTTATAA      4670
GTGACTAAAC  AAATAACTAA  ATAGATGGGG  GTTTCTTTTA  ATATTATGTG      4720
TCCTAATAGT  AGCATTTATT  CAGATGAAAA  ATCAAGGGTT  TTAGTGGACA      4770
AGACAAAAAG  TGGAAAAGTG  AGACCATGGA  GAGAAAAGAA  AATCGCTAAT      4820
GTTGATTACT  TTGAACTTCT  GCATATTCTT  GAATTTAAAA  AGGCTGAAAG      4870
AGTAAAAGAT  TGTGCTGAAA  TATTAGAGTA  TAAACAAAAT  CGTGAAACAG      4920
GCGAAAGAAA  GTTGTATCGA  GTGTGGTTTT  GTAAATCCAG  GCTTTGTCCA      4970
ATGTGCAACT  GGAGGAGAGC  AATGAAACAT  GGCATTCAGT  CACAAAAGGT      5020
TGTTGCTGAA  GTTATTAAAC  AAAAGCCAAC  AGTTCGTTGG  TTGTTTCTCA      5070
CATTAACAGT  TAAAAATGTT  TATGATGGCG  AAGAATTAAA  TAAGAGTTTG      5120
TCAGATATGG  CTCAAGGATT  TCGCCGAATG  ATGCAATATA  AAAAAATTAA      5170
TAAAAATCTT  GTTGGTTTTA  TGCGTGCAAC  GGAAGTGACA  ATAAATAATA      5220
AAGATAATTC  TTATAATCAG  CACATGCATG  TATTGGTATG  TGTGGAACCA      5270
ACTTATTTTA  AGAATACAGA  AAACTACGTG  AATCAAAAC   AATGGATTCA      5320
ATTTTGGAAA  AAGGCAATGA  AATTAGACTA  TGATCCAAAT  GTAAAAGTTC      5370
AAATGATTCG  ACCGAAAAAT  AAATATAAAT  CGGATATACA  ATCGGCAATT      5420
GACGAAACTG  CAAAATATCC  TGTAAAGGAT  ACGGATTTTA  TGACCGATGA      5470
TGAAGAAAAG  AATTTGAAAC  GTTTGTCTGA  TTTGGAGGAA  GGTTTACACC      5520
GTAAAAGGTT  AATCTCCTAT  GGTGGTTTGT  TAAAAGAAAT  ACATAAAAAA      5570
TTAAACCTTG  ATGACACAGA  AGAAGGCGAT  TTGATTCATA  CAGATGATGA      5620
CGAAAAAGCC  GATGAAGATG  GATTTTCTAT  TATTGCAATG  TGGAATTGGG      5670
AACGGAAAAA  TTATTTTATT  AAAGAGTAGT  TCAACAAACG  GGCCAGTTTG      5720
TTGAAGATTA  GATGCTATAA  TTGTTATTAA  AAGGATTGAA  GGATGCTTAG      5770
GAAGACGAGT  TATTAATAGC  TGAATAAGAA  CGGTGCTCTC  CAAATATTCT      5820
TATTTAGAAA  AGCAAATCTA  AAATTATCTG  AAAAGGGAAT  GAGAATAGTG      5870
AATGGACCAA  TAATAATGAC  TAGAGAAGAA  AGAATGAAGA  TTGTTCATGA      5920
AATTAAGGAA  CGAATATTGG  ATAAATATGG  GGATGATGTT  AAGGCTATTG      5970
GTGTTTATGG  CTCTCTTGGT  CGTCAGACTG  ATGGGCCCTA  TTCGGATATT      6020
GAGATGATGT  GTGTCATGTC  AACAGAGGAA  GCAGAGTTCA  GCCATGAATG      6070
GACAACCGGT  GAGTGGAAGG  TGGAAGTGAA  TTTTGATAGC  GAAGAGATTC      6120
TACTAGATTA  TGCATCTCAG  GTGGAATCAG  ATTGGCCGCT  TACACATGGT      6170
CAATTTTTCT  CTATTTTGCC  GATTTATGAT  TCAGGTGGAT  ACTTAGAGAA      6220
AGTGTATCAA  ACTGCTAAAT  CGGTAGAAGC  CCAAACGTTC  CACGATGCGA      6270
TTTGTGCCCT  TATCGTAGAA  GAGCTGTTTG  AATATGCAGG  CAAATGGCGT      6320
AATATTCGTG  TGCAAGGACC  GACAACATTT  CTACCATCCT  TGACTGTACA      6370
GGTAGCAATG  GCAGGTGCCA  TGTTGATTGG  TCTGCATCAT  CGCATCTGTT      6420
```

-continued

```
ATACGACGAG CGCTTCGGTC TTAACTGAAG CAGTTAAGCA ATCAGATCTT      6470
CCTTCAGGTT ATGACCATCT GTGCCAGTTC GTAATGTCTG GTCAACTTTC      6520
CGACTCTGAG AAACTTCTGG AATCGCTAGA GAATTTCTGG AATGGGATTC      6570
AGGAGTGGAC AGAACGACAC GGATATATAG TGGATGTGTC AAAACGCATA      6620
CCATTTTGAA CGATGACCTC TAATAATTGT TAATCATGTT GGTTACGTAT      6670
TTATTAACTT CTCCTAGTAT TAGTAATTAT CATGGCTGTC ATGGCGCATT      6720
AACGGAATAA AGGGTGTGCT TAAATCGGGC CATTTTGCGT AATAAGAAAA      6770
AGGATTAATT ATGAGCGAAT TGAATTAATA ATAAGGTAAT AGATTTACAT      6820
TAGAAAATGA AAGGGGATTT TATGCGTGAG AATGTTACAG TCTATCCCGG      6870
CAATAGTTAC CCTTATTATC AAGATAAGAA AGAAAAGGAT TTTTCGCTAC      6920
GCTCAAATCC TTTAAAAAAA CACAAAAGAC CACATTTTTT AATGTGGTCT      6970
TTATTCTTCA ACTAAAGCAC CCATTAGTTC AACAAACGAA AATTGGATAA      7020
AGTGGGATAT TTTTAAAATA TATATTTATG TTACAGTAAT ATTGACTTTT      7070
AAAAAAGGAT TGATTCTAAT GAAGAAAGCA GACAAGTAAG CCTCCTAAAT      7120
TCACTTTAGA TAAAAATTTA GGAGGCATAT CAAATGAACT TTAATAAAAT      7170
TGATTTAGAC AATTGGAAGA GAAAAGAGAT ATTTAATCAT TATTTGAACC      7220
AACAAACGAC TTTTAGTATA ACCACAGAAA TTGATATTAG TGTTTTATAC      7270
CGAAACATAA AACAAGAAGG ATATAAATTT TACCCTGCAT TTATTTTCTT      7320
AGTGACAAGG GTGATAAACT CAAATACAGC TTTTAGAACT GGTTACAATA      7370
GCGACGGAGA GTTAGGTTAT TGGGATAAGT TAGAGCCACT TTATACAATT      7420
TTTGATGGTG TATCTAAAAC ATTCTCTGGT ATTTGGACTC CTGTAAAGAA      7470
TGACTTCAAA GAGTTTTATG ATTTATACCT TTCTGATGTA GAGAAATATA      7520
ATGGTTCGGG GAAATTGTTT CCCAAAACAC CTATACCTGA AAATGCTTTT      7570
TCTCTTTCTA TTATTCCATG GACTTCATTT ACTGGGTTTA ACTTAAATAT      7620
CAATAATAAT AGTAATTACC TTCTACCCAT TATTACAGCA GGAAAATTCA      7670
TTAATAAAGG TAATTCAATA TATTTACCGC TATCTTTACA GGTACATCAT      7720
TCTGTTTGTG ATGGTTATCA TGCAGGATTG TTTATGAACT CTATTCAGGA      7770
ATTGTCAGAT AGGCCTAATG ACTGGCTTTT ATAATATGAG ATAATGCCGA      7820
CTGTACTTTT TACAGTCGGT TTTCTAATGT CACTAACCTG CCCCGTTAGT      7870
TGAAGAAGGT TTTTATATTA CAGCTCCAGA TCCATATCCT TCTTTTTCTG      7920
AACCGACTTC TCCTTTTTCG CTTCTTTATT CCAATTGCTT TATTGACGTT      7970
GAGCCTCGGA ACCCNTATAG TGTGTTATAC TTTACTTGGA AGTGGTTGCC      8020
GGAAAGAGCG AAAATGCCTC ACATTTGTGC CACCTAAAAA GGAGCGATTT      8070
ACATATGAGT TATGCAGTTT GTAGAATGCA AAAAGTGAAA TCAGGATCN      8119
```

( 2 ) INFORMATION FOR SEQ ID NO:2:

( i ) SEQUENCE CHARACTERISTICS:
        ( A ) LENGTH: 382 amino acids
        ( B ) TYPE: Amino Acid
        ( D ) TOPOLOGY: Linear ( x i ) SEQUENCE DESCRIPTION: SEQ ID NO:2:

Val Arg Gly Lys Lys Val Trp Ile Ser Leu Leu Phe Ala Leu Ala

-continued

| | -107 | | -105 | | | | -100 | | | | | -95 | | |
|---|---|---|---|---|---|---|---|---|---|---|---|---|---|---|
| Leu | Ile | Phe | Thr | Met | Ala | Phe | Gly | Ser | Thr | Ser | Ser | Ala | Gln | Ala |
| | | -90 | | | | -85 | | | | | | -80 | | |
| Ala | Gly | Lys | Ser | Asn | Gly | Glu | Lys | Lys | Tyr | Ile | Val | Gly | Phe | Lys |
| | | -75 | | | | -70 | | | | | | -65 | | |
| Gln | Thr | Met | Ser | Thr | Met | Ser | Ala | Ala | Lys | Lys | Lys | Asp | Val | Ile |
| | | -60 | | | | -55 | | | | | | -50 | | |
| Ser | Glu | Lys | Gly | Gly | Lys | Val | Gln | Lys | Gln | Phe | Lys | Tyr | Val | Asp |
| | | -45 | | | | -40 | | | | | | -35 | | |
| Ala | Ala | Ser | Ala | Thr | Leu | Asn | Glu | Lys | Ala | Val | Lys | Glu | Leu | Lys |
| | | -30 | | | | -25 | | | | | | -20 | | |
| Lys | Asp | Pro | Ser | Val | Ala | Tyr | Val | Glu | Glu | Asp | His | Val | Ala | His |
| | | -15 | | | | -10 | | | | | | -5 | | |
| Ala | Tyr | Ala | Gln | Ser | Val | Pro | Tyr | Gly | Val | Ser | Gln | Ile | Lys | Ala |
| | | 1 | | | | 5 | | | | | | 10 | | |
| Pro | Ala | Leu | His | Ser | Gln | Gly | Tyr | Thr | Gly | Ser | Asn | Val | Lys | Val |
| | | 15 | | | | 20 | | | | | | 25 | | |
| Ala | Val | Ile | Asp | Ser | Gly | Ile | Asp | Ser | Ser | His | Pro | Asp | Leu | Lys |
| | | 30 | | | | 35 | | | | | | 40 | | |
| Val | Ala | Gly | Gly | Ala | Ser | Met | Val | Pro | Ser | Glu | Thr | Asn | Pro | Phe |
| | | 45 | | | | 50 | | | | | | 55 | | |
| Gln | Asp | Asn | Asp | Ser | His | Gly | Thr | His | Val | Ala | Gly | Thr | Val | Ala |
| | | 60 | | | | 65 | | | | | | 70 | | |
| Ala | Leu | Asn | Asn | Ser | Ile | Gly | Val | Leu | Gly | Val | Ala | Pro | Ser | Ala |
| | | 75 | | | | 80 | | | | | | 85 | | |
| Ser | Leu | Tyr | Ala | Val | Lys | Val | Leu | Gly | Ala | Asp | Gly | Ser | Gly | Gln |
| | | 90 | | | | 95 | | | | | | 100 | | |
| Tyr | Ser | Trp | Ile | Ile | Asn | Gly | Ile | Glu | Trp | Ala | Ile | Ala | Asn | Asn |
| | | 105 | | | | 110 | | | | | | 115 | | |
| Met | Asp | Val | Ile | Asn | Met | Ser | Leu | Gly | Gly | Pro | Ser | Gly | Ser | Ala |
| | | 120 | | | | 125 | | | | | | 130 | | |
| Ala | Leu | Lys | Ala | Ala | Val | Asp | Lys | Ala | Val | Ala | Ser | Gly | Val | Val |
| | | 135 | | | | 140 | | | | | | 145 | | |
| Val | Val | Ala | Ala | Ala | Gly | Asn | Glu | Gly | Thr | Ser | Gly | Ser | Ser | Ser |
| | | 150 | | | | 155 | | | | | | 160 | | |
| Thr | Val | Asp | Tyr | Pro | Gly | Lys | Tyr | Pro | Ser | Val | Ile | Ala | Val | Gly |
| | | 165 | | | | 170 | | | | | | 175 | | |
| Ala | Val | Asp | Ser | Ser | Asn | Gln | Arg | Ala | Ser | Phe | Ser | Ser | Val | Gly |
| | | 180 | | | | 185 | | | | | | 190 | | |
| Pro | Glu | Leu | Asp | Val | Met | Ala | Pro | Gly | Val | Ser | Ile | Gln | Ser | Thr |
| | | 195 | | | | 200 | | | | | | 205 | | |
| Leu | Pro | Gly | Asn | Lys | Tyr | Gly | Ala | Tyr | Asn | Gly | Thr | Ser | Met | Ala |
| | | 210 | | | | 215 | | | | | | 220 | | |
| Ser | Pro | His | Val | Ala | Gly | Ala | Ala | Ala | Leu | Ile | Leu | Ser | Lys | His |
| | | 225 | | | | 230 | | | | | | 235 | | |
| Pro | Asn | Trp | Thr | Asn | Thr | Gln | Val | Arg | Ser | Ser | Leu | Glu | Asn | Thr |
| | | 240 | | | | 245 | | | | | | 250 | | |
| Thr | Thr | Lys | Leu | Gly | Asp | Ser | Phe | Tyr | Tyr | Gly | Lys | Gly | Leu | Ile |
| | | 255 | | | | 260 | | | | | | 265 | | |
| Asn | Val | Gln | Ala | Ala | Ala | Gln | | | | | | | | |
| | | 270 | | | | 275 | | | | | | | | |

( 2 ) INFORMATION FOR SEQ ID NO:3:

( i ) SEQUENCE CHARACTERISTICS:
  ( A ) LENGTH: 7 amino acids
  ( B ) TYPE: Amino Acid
  ( D ) TOPOLOGY: Linear ( x i ) SEQUENCE DESCRIPTION: SEQ ID NO:3:

Ser Leu Gly Gly Pro Ser Gly
 1           5       7

( 2 ) INFORMATION FOR SEQ ID NO:4:

( i ) SEQUENCE CHARACTERISTICS:
    ( A ) LENGTH: 7 amino acids
    ( B ) TYPE: Amino Acid
    ( D ) TOPOLOGY: Linear ( x i ) SEQUENCE DESCRIPTION: SEQ ID NO:4:

Ala Ala Ala Gly Asn Glu Gly
 1           5       7

( 2 ) INFORMATION FOR SEQ ID NO:5:

( i ) SEQUENCE CHARACTERISTICS:
    ( A ) LENGTH: 6 amino acids
    ( B ) TYPE: Amino Acid
    ( D ) TOPOLOGY: Linear ( x i ) SEQUENCE DESCRIPTION: SEQ ID NO:5:

Ser Thr Val Gly Tyr Pro
 1           5   6

( 2 ) INFORMATION FOR SEQ ID NO:6:

( i ) SEQUENCE CHARACTERISTICS:
    ( A ) LENGTH: 7 amino acids
    ( B ) TYPE: Amino Acid
    ( D ) TOPOLOGY: Linear ( x i ) SEQUENCE DESCRIPTION: SEQ ID NO:6:

Ser Trp Gly Pro Ala Asp Asp
 1           5       7

( 2 ) INFORMATION FOR SEQ ID NO:7:

( i ) SEQUENCE CHARACTERISTICS:
    ( A ) LENGTH: 7 amino acids
    ( B ) TYPE: Amino Acid
    ( D ) TOPOLOGY: Linear ( x i ) SEQUENCE DESCRIPTION: SEQ ID NO:7:

Phe Ala Ser Gly Asn Gly Gly
 1           5       7

( 2 ) INFORMATION FOR SEQ ID NO:8:

( i ) SEQUENCE CHARACTERISTICS:
    ( A ) LENGTH: 7 amino acids
    ( B ) TYPE: Amino Acid
    ( D ) TOPOLOGY: Linear ( x i ) SEQUENCE DESCRIPTION: SEQ ID NO:8:

Cys Asn Tyr Asp Gly Tyr Thr
 1           5       7

( 2 ) INFORMATION FOR SEQ ID NO:9:

( i ) SEQUENCE CHARACTERISTICS:
    ( A ) LENGTH: 7 amino acids ( B ) TYPE: Amino Acid
( D ) TOPOLOGY: Linear ( x i ) SEQUENCE DESCRIPTION: SEQ ID NO:9:

Ser Trp Gly Pro Glu Asp Asp
1               5       7

( 2 ) INFORMATION FOR SEQ ID NO:10:

( i ) SEQUENCE CHARACTERISTICS:
( A ) LENGTH: 7 amino acids
( B ) TYPE: Amino Acid
( D ) TOPOLOGY: Linear ( x i ) SEQUENCE DESCRIPTION: SEQ ID NO:10:

Trp Ala Ser Gly Asn Gly Gly
1               5       7

( 2 ) INFORMATION FOR SEQ ID NO:11:

( i ) SEQUENCE CHARACTERISTICS:
( A ) LENGTH: 7 amino acids
( B ) TYPE: Amino Acid
( D ) TOPOLOGY: Linear ( x i ) SEQUENCE DESCRIPTION: SEQ ID NO:11:

Cys Asn Cys Asp Gly Tyr Thr
1               5       7

( 2 ) INFORMATION FOR SEQ ID NO:12:

( i ) SEQUENCE CHARACTERISTICS:
( A ) LENGTH: 7 amino acids
( B ) TYPE: Amino Acid
( D ) TOPOLOGY: Linear ( x i ) SEQUENCE DESCRIPTION: SEQ ID NO:12:

Trp Ala Ser Gly Asp Gly Gly
1               5       7

( 2 ) INFORMATION FOR SEQ ID NO:13:

( i ) SEQUENCE CHARACTERISTICS:
( A ) LENGTH: 7 amino acids
( B ) TYPE: Amino Acid
( D ) TOPOLOGY: Linear ( x i ) SEQUENCE DESCRIPTION: SEQ ID NO:13:

Cys Asn Cys Asp Gly Tyr Ala
1               5       7

( 2 ) INFORMATION FOR SEQ ID NO:14:

( i ) SEQUENCE CHARACTERISTICS:
( A ) LENGTH: 6 amino acids
( B ) TYPE: Amino Acid
( D ) TOPOLOGY: Linear ( x i ) SEQUENCE DESCRIPTION: SEQ ID NO:14:

Val Ile Asp Ser Gly Ile
1               5   6

( 2 ) INFORMATION FOR SEQ ID NO:15:

( i ) SEQUENCE CHARACTERISTICS:
( A ) LENGTH: 5 amino acids
( B ) TYPE: Amino Acid
( D ) TOPOLOGY: Linear ( x i ) SEQUENCE DESCRIPTION: SEQ ID NO:15:

Asp Asn Asn Ser His
 1               5

( 2 ) INFORMATION FOR SEQ ID NO:16:

( i ) SEQUENCE CHARACTERISTICS:
　　　　( A ) LENGTH: 6 amino acids
　　　　( B ) TYPE: Amino Acid
　　　　( D ) TOPOLOGY: Linear ( x i ) SEQUENCE DESCRIPTION: SEQ ID NO:16:

Ile Val Asp Asp Gly Leu
 1               5   6

( 2 ) INFORMATION FOR SEQ ID NO:17:

( i ) SEQUENCE CHARACTERISTICS:
　　　　( A ) LENGTH: 5 amino acids
　　　　( B ) TYPE: Amino Acid
　　　　( D ) TOPOLOGY: Linear ( x i ) SEQUENCE DESCRIPTION: SEQ ID NO:17:

Ser Asp Asp Tyr His
 1               5

( 2 ) INFORMATION FOR SEQ ID NO:18:

( i ) SEQUENCE CHARACTERISTICS:
　　　　( A ) LENGTH: 6 amino acids
　　　　( B ) TYPE: Amino Acid
　　　　( D ) TOPOLOGY: Linear ( x i ) SEQUENCE DESCRIPTION: SEQ ID NO:18:

Ile Leu Asp Asp Gly Ile
 1               5   6

( 2 ) INFORMATION FOR SEQ ID NO:19:

( i ) SEQUENCE CHARACTERISTICS:
　　　　( A ) LENGTH: 5 amino acids
　　　　( B ) TYPE: Amino Acid
　　　　( D ) TOPOLOGY: Linear ( x i ) SEQUENCE DESCRIPTION: SEQ ID NO:19:

Asn Asp Asn Arg His
 1               5

( 2 ) INFORMATION FOR SEQ ID NO:20:

( i ) SEQUENCE CHARACTERISTICS:
　　　　( A ) LENGTH: 6 amino acids
　　　　( B ) TYPE: Amino Acid
　　　　( D ) TOPOLOGY: Linear ( x i ) SEQUENCE DESCRIPTION: SEQ ID NO:20:

Ile Met Asp Asp Gly Ile
 1               5   6

( 2 ) INFORMATION FOR SEQ ID NO:21:

( i ) SEQUENCE CHARACTERISTICS:
　　　　( A ) LENGTH: 5 amino acids
　　　　( B ) TYPE: Amino Acid
　　　　( D ) TOPOLOGY: Linear ( x i ) SEQUENCE DESCRIPTION: SEQ ID NO:21:

Trp Phe Asn Ser His
1               5

( 2 ) INFORMATION FOR SEQ ID NO:22:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:22:

GCGGTTATCG ACGACGGTAT CGATTCT        27

( 2 ) INFORMATION FOR SEQ ID NO:23:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:23:

GCGGTTATCG ACAAAGGTAT CGATTCT        27

( 2 ) INFORMATION FOR SEQ ID NO:24:

( i ) SEQUENCE CHARACTERISTICS:
        ( A ) LENGTH: 27 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:24:

GCGGTTATCG ACGAAGGTAT CGATTCT        27

( 2 ) INFORMATION FOR SEQ ID NO:25:

( i ) SEQUENCE CHARACTERISTICS:
        ( A ) LENGTH: 23 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:25:

CCAAGACAAC GACTCTCACG GAA        23

( 2 ) INFORMATION FOR SEQ ID NO:26:

( i ) SEQUENCE CHARACTERISTICS:
        ( A ) LENGTH: 23 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:26:

CCAAGACAAC AGCTCTCACG GAA        23

( 2 ) INFORMATION FOR SEQ ID NO:27:

( i ) SEQUENCE CHARACTERISTICS:
        ( A ) LENGTH: 23 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:27:

CCAAGACAAC AAATCTCACG GAA 23

( 2 ) INFORMATION FOR SEQ ID NO:28:

( i ) SEQUENCE CHARACTERISTICS:
  ( A ) LENGTH: 42 base pairs
  ( B ) TYPE: Nucleic Acid
  ( C ) STRANDEDNESS: Single
  ( D ) TOPOLOGY: Linear ( x i ) SEQUENCE DESCRIPTION: SEQ ID NO:28:

CACTTCCGGC AGCTCGTCGA CAGTGGACTA CCCTGGCAAA TA 42

( 2 ) INFORMATION FOR SEQ ID NO:29:

( i ) SEQUENCE CHARACTERISTICS:
  ( A ) LENGTH: 42 base pairs
  ( B ) TYPE: Nucleic Acid
  ( C ) STRANDEDNESS: Single
  ( D ) TOPOLOGY: Linear ( x i ) SEQUENCE DESCRIPTION: SEQ ID NO:29:

CACTTCCGGC AGCTCGTCGA CAGTGGAGTA CCCTGGCAAA TA 42

( 2 ) INFORMATION FOR SEQ ID NO:30:

( i ) SEQUENCE CHARACTERISTICS:
  ( A ) LENGTH: 41 base pairs
  ( B ) TYPE: Nucleic Acid
  ( C ) STRANDEDNESS: Single
  ( D ) TOPOLOGY: Linear ( x i ) SEQUENCE DESCRIPTION: SEQ ID NO:30:

TTAACATGAG CCTCGGCCCA GCTAGCGGTT CTGCTGCTTT A 41

( 2 ) INFORMATION FOR SEQ ID NO:31:

( i ) SEQUENCE CHARACTERISTICS:
  ( A ) LENGTH: 43 base pairs
  ( B ) TYPE: Nucleic Acid
  ( C ) STRANDEDNESS: Single
  ( D ) TOPOLOGY: Linear ( x i ) SEQUENCE DESCRIPTION: SEQ ID NO:31:

TTAACATGAG CCTCGGCCCC GCGGATGATT CTGCTGCTTT AAA 43

( 2 ) INFORMATION FOR SEQ ID NO:32:

( i ) SEQUENCE CHARACTERISTICS:
  ( A ) LENGTH: 47 base pairs
  ( B ) TYPE: Nucleic Acid
  ( C ) STRANDEDNESS: Single
  ( D ) TOPOLOGY: Linear ( x i ) SEQUENCE DESCRIPTION: SEQ ID NO:32:

CGGCAGCTCA AGCAACGATG GCTATCCTGG CAAATACCCT TCTGTCA 47

( 2 ) INFORMATION FOR SEQ ID NO:33:

( i ) SEQUENCE CHARACTERISTICS:
  ( A ) LENGTH: 44 base pairs
  ( B ) TYPE: Nucleic Acid
  ( C ) STRANDEDNESS: Single
  ( D ) TOPOLOGY: Linear ( x i ) SEQUENCE DESCRIPTION: SEQ ID NO:33:

ACTTCCGGCA GCTCTTCGAA CTACGACGGG TACCTGGCA AATA 44

( 2 ) INFORMATION FOR SEQ ID NO:34:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:34:

Asn Leu Thr Ala Arg
1                   5

( 2 ) INFORMATION FOR SEQ ID NO:35:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:35:

Asn Leu Met Arg Lys
1                   5

( 2 ) INFORMATION FOR SEQ ID NO:36:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:36:

Thr Ala Ser Arg Arg
1                   5

( 2 ) INFORMATION FOR SEQ ID NO:37:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:37:

Leu Thr Arg Arg Ser
1                   5

( 2 ) INFORMATION FOR SEQ ID NO:38:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:38:

Ala Leu Ser Arg Lys
1                   5

( 2 ) INFORMATION FOR SEQ ID NO:39:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:39:

Leu Met Leu Arg Lys
1                   5

( 2 ) INFORMATION FOR SEQ ID NO:40:

( i ) SEQUENCE CHARACTERISTICS:
( A ) LENGTH: 5 amino acids
( B ) TYPE: Amino Acid
( D ) TOPOLOGY: Linear ( x i ) SEQUENCE DESCRIPTION: SEQ ID NO:40:

Ala Ser Thr His Phe
 1               5

( 2 ) INFORMATION FOR SEQ ID NO:41:

( i ) SEQUENCE CHARACTERISTICS:
( A ) LENGTH: 5 amino acids
( B ) TYPE: Amino Acid
( D ) TOPOLOGY: Linear ( x i ) SEQUENCE DESCRIPTION: SEQ ID NO:41:

Gln Lys Pro Asn Phe
 1               5

( 2 ) INFORMATION FOR SEQ ID NO:42:

( i ) SEQUENCE CHARACTERISTICS:
( A ) LENGTH: 5 amino acids
( B ) TYPE: Amino Acid
( D ) TOPOLOGY: Linear ( x i ) SEQUENCE DESCRIPTION: SEQ ID NO:42:

Arg Lys Pro Thr His
 1               5

( 2 ) INFORMATION FOR SEQ ID NO:43:

( i ) SEQUENCE CHARACTERISTICS:
( A ) LENGTH: 5 amino acids
( B ) TYPE: Amino Acid
( D ) TOPOLOGY: Linear ( x i ) SEQUENCE DESCRIPTION: SEQ ID NO:43:

Ile Gln Gln Gln Tyr
 1               5

( 2 ) INFORMATION FOR SEQ ID NO:44:

( i ) SEQUENCE CHARACTERISTICS:
( A ) LENGTH: 5 amino acids
( B ) TYPE: Amino Acid
( D ) TOPOLOGY: Linear ( x i ) SEQUENCE DESCRIPTION: SEQ ID NO:44:

Arg Pro Gly Ala Met
 1               5

( 2 ) INFORMATION FOR SEQ ID NO:45:

( i ) SEQUENCE CHARACTERISTICS:
( A ) LENGTH: 5 amino acids
( B ) TYPE: Amino Acid
( D ) TOPOLOGY: Linear ( x i ) SEQUENCE DESCRIPTION: SEQ ID NO:45:

Gln Gly Glu Leu Pro
 1               5

( 2 ) INFORMATION FOR SEQ ID NO:46:

( i ) SEQUENCE CHARACTERISTICS:

(A) LENGTH: 5 amino acids
(B) TYPE: Amino Acid
(D) TOPOLOGY: Linear (xi) SEQUENCE DESCRIPTION: SEQ ID NO:46:

Ala Pro Asp Pro Thr
 1               5

(2) INFORMATION FOR SEQ ID NO:47:

(i) SEQUENCE CHARACTERISTICS:
(A) LENGTH: 5 amino acids
(B) TYPE: Amino Acid
(D) TOPOLOGY: Linear (xi) SEQUENCE DESCRIPTION: SEQ ID NO:47:

Gln Leu Leu Glu His
 1               5

(2) INFORMATION FOR SEQ ID NO:48:

(i) SEQUENCE CHARACTERISTICS:
(A) LENGTH: 5 amino acids
(B) TYPE: Amino Acid
(D) TOPOLOGY: Linear (xi) SEQUENCE DESCRIPTION: SEQ ID NO:48:

Val Asn Asn Asn His
 1               5

(2) INFORMATION FOR SEQ ID NO:49:

(i) SEQUENCE CHARACTERISTICS:
(A) LENGTH: 5 amino acids
(B) TYPE: Amino Acid
(D) TOPOLOGY: Linear (xi) SEQUENCE DESCRIPTION: SEQ ID NO:49:

Ala Gln Ser Asn Leu
 1               5

(2) INFORMATION FOR SEQ ID NO:50:

(i) SEQUENCE CHARACTERISTICS:
(A) LENGTH: 5 amino acids
(B) TYPE: Amino Acid
(D) TOPOLOGY: Linear (xi) SEQUENCE DESCRIPTION: SEQ ID NO:50:

Thr Ala Ser Arg Arg
 1               5

(2) INFORMATION FOR SEQ ID NO:51:

(i) SEQUENCE CHARACTERISTICS:
(A) LENGTH: 6 amino acids
(B) TYPE: Amino Acid
(D) TOPOLOGY: Linear (xi) SEQUENCE DESCRIPTION: SEQ ID NO:51:

His His His His His His
 1               5   6

(2) INFORMATION FOR SEQ ID NO:52:

(i) SEQUENCE CHARACTERISTICS:
(A) LENGTH: 4 amino acids
(B) TYPE: Amino Acid (D) TOPOLOGY: Linear (x i) SEQUENCE DESCRIPTION: SEQ ID NO:52:

Leu Met Arg Lys
1               4

(2) INFORMATION FOR SEQ ID NO:53:

(i) SEQUENCE CHARACTERISTICS:
     (A) LENGTH: 4 amino acids
     (B) TYPE: Amino Acid
     (D) TOPOLOGY: Linear (x i) SEQUENCE DESCRIPTION: SEQ ID NO:53:

Leu Thr Ala Arg
1               4

(2) INFORMATION FOR SEQ ID NO:54:

(i) SEQUENCE CHARACTERISTICS:
     (A) LENGTH: 4 amino acids
     (B) TYPE: Amino Acid
     (D) TOPOLOGY: Linear (x i) SEQUENCE DESCRIPTION: SEQ ID NO:54:

Gly Pro Gly Gly
1               4

(2) INFORMATION FOR SEQ ID NO:55:

(i) SEQUENCE CHARACTERISTICS:
     (A) LENGTH: 5 amino acids
     (B) TYPE: Amino Acid
     (D) TOPOLOGY: Linear (x i) SEQUENCE DESCRIPTION: SEQ ID NO:55:

Gly Leu Met Arg Lys
1                   5

(2) INFORMATION FOR SEQ ID NO:56:

(i) SEQUENCE CHARACTERISTICS:
     (A) LENGTH: 4 amino acids
     (B) TYPE: Amino Acid
     (D) TOPOLOGY: Linear (x i) SEQUENCE DESCRIPTION: SEQ ID NO:56:

Ala Ala Pro Phe
1               4

(2) INFORMATION FOR SEQ ID NO:57:

(i) SEQUENCE CHARACTERISTICS:
     (A) LENGTH: 13 amino acids
     (B) TYPE: Amino Acid
     (D) TOPOLOGY: Linear (x i) SEQUENCE DESCRIPTION: SEQ ID NO:57:

Gly Pro Gly Gly Xaa Xaa Xaa Xaa Xaa Gly Gly Pro Gly
1               5                   10              13

(2) INFORMATION FOR SEQ ID NO:58:

(i) SEQUENCE CHARACTERISTICS:
     (A) LENGTH: 4 amino acids
     (B) TYPE: Amino Acid
     (D) TOPOLOGY: Linear ( x i ) SEQUENCE DESCRIPTION: SEQ ID NO:58:

Ala  Ala  Pro  Lys
 1                4

( 2 ) INFORMATION FOR SEQ ID NO:59:

( i ) SEQUENCE CHARACTERISTICS:
      ( A ) LENGTH: 4 amino acids
      ( B ) TYPE: Amino Acid
      ( D ) TOPOLOGY: Linear ( x i ) SEQUENCE DESCRIPTION: SEQ ID NO:59:

Ala  Ala  Pro  Arg
 1                4

( 2 ) INFORMATION FOR SEQ ID NO:60:

( i ) SEQUENCE CHARACTERISTICS:
      ( A ) LENGTH: 4 amino acids
      ( B ) TYPE: Amino Acid
      ( D ) TOPOLOGY: Linear ( x i ) SEQUENCE DESCRIPTION: SEQ ID NO:60:

Ala  Ala  Pro  Met
 1                4

( 2 ) INFORMATION FOR SEQ ID NO:61:

( i ) SEQUENCE CHARACTERISTICS:
      ( A ) LENGTH: 4 amino acids
      ( B ) TYPE: Amino Acid
      ( D ) TOPOLOGY: Linear ( x i ) SEQUENCE DESCRIPTION: SEQ ID NO:61:

Ala  Ala  Pro  Gln
 1                4

( 2 ) INFORMATION FOR SEQ ID NO:62:

( i ) SEQUENCE CHARACTERISTICS:
      ( A ) LENGTH: 4 amino acids
      ( B ) TYPE: Amino Acid
      ( D ) TOPOLOGY: Linear ( x i ) SEQUENCE DESCRIPTION: SEQ ID NO:62:

Ala  Ala  Lys  Phe
 1                4

( 2 ) INFORMATION FOR SEQ ID NO:63:

( i ) SEQUENCE CHARACTERISTICS:
      ( A ) LENGTH: 4 amino acids
      ( B ) TYPE: Amino Acid
      ( D ) TOPOLOGY: Linear ( x i ) SEQUENCE DESCRIPTION: SEQ ID NO:63:

Ala  Ala  Ala  Phe
 1                4

( 2 ) INFORMATION FOR SEQ ID NO:64:

( i ) SEQUENCE CHARACTERISTICS:
      ( A ) LENGTH: 4 amino acids
      ( B ) TYPE: Amino Acid
      ( D ) TOPOLOGY: Linear ( x i ) SEQUENCE DESCRIPTION: SEQ ID NO:64:

Ala Ala Arg Phe
1           4

( 2 ) INFORMATION FOR SEQ ID NO:65:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:65:

Ala Ala Asp Phe
1           4

( 2 ) INFORMATION FOR SEQ ID NO:66:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:66:

Ala Ala Lys Lys
1           4

( 2 ) INFORMATION FOR SEQ ID NO:67:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:67:

Ala Ala Lys Arg
1           4

( 2 ) INFORMATION FOR SEQ ID NO:68:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:68:

Ala Ala Lys Phe
1           4

( 2 ) INFORMATION FOR SEQ ID NO:69:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:69:

Ala Ala Pro Xaa
1           4

( 2 ) INFORMATION FOR SEQ ID NO:70:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:70:

Ala Ala Xaa Phe
1           4

( 2 ) INFORMATION FOR SEQ ID NO:71:

( i ) SEQUENCE CHARACTERISTICS:
        ( A ) LENGTH: 5 amino acids
        ( B ) TYPE: Amino Acid
        ( D ) TOPOLOGY: Linear ( x i ) SEQUENCE DESCRIPTION: SEQ ID NO:71:

```
Ala  Ala  Xaa  Xaa  Xaa
 1                    5
```

( 2 ) INFORMATION FOR SEQ ID NO:72:

( i ) SEQUENCE CHARACTERISTICS:
        ( A ) LENGTH: 275 amino acids
        ( B ) TYPE: Amino Acid
        ( D ) TOPOLOGY: Linear ( x i ) SEQUENCE DESCRIPTION: SEQ ID NO:72:

```
Ala  Gln  Ser  Val  Pro  Tyr  Gly  Val  Ser  Gln  Ile  Lys  Ala  Pro  Ala
 1                   5                        10                       15

Leu  His  Ser  Gln  Gly  Tyr  Thr  Gly  Ser  Asn  Val  Lys  Val  Ala  Val
                    20                        25                       30

Ile  Asp  Ser  Gly  Ile  Asp  Ser  Ser  His  Pro  Asp  Leu  Lys  Val  Ala
                    35                        40                       45

Gly  Gly  Ala  Ser  Met  Val  Pro  Ser  Glu  Thr  Asn  Pro  Phe  Gln  Asp
                    50                        55                       60

Asn  Asp  Ser  His  Gly  Thr  His  Val  Ala  Gly  Thr  Val  Ala  Ala  Leu
                    65                        70                       75

Asn  Asn  Ser  Ile  Gly  Val  Leu  Gly  Val  Ala  Pro  Ser  Ala  Ser  Leu
                    80                        85                       90

Tyr  Ala  Val  Lys  Val  Leu  Gly  Ala  Asp  Gly  Ser  Gly  Gln  Tyr  Ser
                    95                       100                      105

Trp  Ile  Ile  Asn  Gly  Ile  Glu  Trp  Ala  Ile  Ala  Asn  Asn  Met  Asp
                   110                       115                      120

Val  Ile  Asn  Met  Ser  Leu  Gly  Gly  Pro  Ser  Gly  Ser  Ala  Ala  Leu
                   125                       130                      135

Lys  Ala  Ala  Val  Asp  Lys  Ala  Val  Ala  Ser  Gly  Val  Val  Val  Val
                   140                       145                      150

Ala  Ala  Ala  Gly  Asn  Glu  Gly  Thr  Ser  Gly  Ser  Ser  Ser  Thr  Val
                   155                       160                      165

Asp  Tyr  Pro  Gly  Lys  Tyr  Pro  Ser  Val  Ile  Ala  Val  Gly  Ala  Val
                   170                       175                      180

Asp  Ser  Ser  Asn  Gln  Arg  Ala  Ser  Phe  Ser  Ser  Val  Gly  Pro  Glu
                   185                       190                      195

Leu  Asp  Val  Met  Ala  Pro  Gly  Val  Ser  Ile  Gln  Ser  Thr  Leu  Pro
                   200                       205                      210

Gly  Asn  Lys  Tyr  Gly  Ala  Tyr  Asn  Gly  Thr  Ser  Met  Ala  Ser  Pro
                   215                       220                      225

His  Val  Ala  Gly  Ala  Ala  Ala  Leu  Ile  Leu  Ser  Lys  His  Pro  Asn
                   230                       235                      240

Trp  Thr  Asn  Thr  Gln  Val  Arg  Ser  Ser  Leu  Glu  Asn  Thr  Thr  Thr
                   245                       250                      255

Lys  Leu  Gly  Asp  Ser  Phe  Tyr  Tyr  Gly  Lys  Gly  Leu  Ile  Asn  Val
                   260                       265                      270

Gln  Ala  Ala  Ala  Gln
                   275
```

( 2 ) INFORMATION FOR SEQ ID NO:73:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:73:

```
Arg  Val  Arg  Arg
 1              4
```

( 2 ) INFORMATION FOR SEQ ID NO:74:

( i ) SEQUENCE CHARACTERISTICS:
        ( A ) LENGTH: 275 amino acids
        ( B ) TYPE: Amino Acid
        ( D ) TOPOLOGY: Linear ( x i ) SEQUENCE DESCRIPTION: SEQ ID NO:74:

```
Ala  Gln  Ser  Val  Pro  Tyr  Gly  Val  Ser  Gln  Ile  Lys  Ala  Pro  Ala
 1                  5                        10                       15

Leu  His  Ser  Gln  Gly  Tyr  Thr  Gly  Ser  Asn  Val  Lys  Val  Ala  Val
                    20                       25                       30

Ile  Asp  Ser  Gly  Ile  Asp  Ser  Ser  His  Pro  Asp  Leu  Lys  Val  Ala
                    35                       40                       45

Gly  Gly  Ala  Ser  Met  Val  Pro  Ser  Glu  Thr  Asn  Pro  Phe  Gln  Asp
                    50                       55                       60

Asn  Asn  Ser  His  Gly  Thr  His  Val  Ala  Gly  Thr  Val  Ala  Ala  Leu
                    65                       70                       75

Asn  Asn  Ser  Ile  Gly  Val  Leu  Gly  Val  Ala  Pro  Ser  Ala  Ser  Leu
                    80                       85                       90

Tyr  Ala  Val  Lys  Val  Leu  Gly  Ala  Asp  Gly  Ser  Gly  Gln  Tyr  Ser
                    95                       100                      105

Trp  Ile  Ile  Asn  Gly  Ile  Glu  Trp  Ala  Ile  Ala  Asn  Asn  Met  Asp
                    110                      115                      120

Val  Ile  Asn  Met  Ser  Leu  Gly  Gly  Pro  Ser  Gly  Ser  Ala  Ala  Leu
                    125                      130                      135

Lys  Ala  Ala  Val  Asp  Lys  Ala  Val  Ala  Ser  Gly  Val  Val  Val  Val
                    140                      145                      150

Ala  Ala  Ala  Gly  Asn  Glu  Gly  Thr  Ser  Gly  Ser  Ser  Ser  Thr  Val
                    155                      160                      165

Gly  Tyr  Pro  Gly  Lys  Tyr  Pro  Ser  Val  Ile  Ala  Val  Gly  Ala  Val
                    170                      175                      180

Asp  Ser  Ser  Asn  Gln  Arg  Ala  Ser  Phe  Ser  Ser  Val  Gly  Pro  Glu
                    185                      190                      195

Leu  Asp  Val  Met  Ala  Pro  Gly  Val  Ser  Ile  Gln  Ser  Thr  Leu  Pro
                    200                      205                      210

Gly  Asn  Lys  Tyr  Gly  Ala  Tyr  Asn  Gly  Thr  Ser  Met  Ala  Ser  Pro
                    215                      220                      225

His  Val  Ala  Gly  Ala  Ala  Ala  Leu  Ile  Leu  Ser  Lys  His  Pro  Asn
                    230                      235                      240

Trp  Thr  Asn  Thr  Gln  Val  Arg  Ser  Ser  Leu  Glu  Asn  Thr  Thr  Thr
                    245                      250                      255

Lys  Leu  Gly  Asp  Ser  Phe  Tyr  Tyr  Gly  Lys  Gly  Leu  Ile  Asn  Val
                    260                      265                      270

Gln  Ala  Ala  Ala  Gln
```

-continued

275

What is claimed is:

1. An isolated subtilisin having substrate specificity for peptide substrates having basic amino acids at the $P_2$ and $P_1$ positions of the substrate, said subtilisin-type serine protease having a negatively charged amino acid at an amino acid residue equivalent to Asn 62 and Gly 166 of the subtilisin having the amino acid sequence of SEQ ID NO: 74 naturally produced by *Bacillus amyloliquefaciens*.

* * * * *